(12) United States Patent
Sugiyama et al.

(10) Patent No.: US 6,589,445 B2
(45) Date of Patent: Jul. 8, 2003

(54) LIGHT-REACTION TYPE OPTICALLY ACTIVE COMPOUND, LIGHT-REACTION TYPE CHIRAL AGENT, LIQUID CRYSTAL COMPOSITION, LIQUID CRYSTAL COLOR FILTER, OPTICAL FILM, RECORDING MEDIUM, AND METHOD OF CHANGING TWIST STRUCTURE OF LIQUID CRYSTAL

(75) Inventors: Takekatsu Sugiyama, Shizuoka-ken (JP); Mitsuyoshi Ichihashi, Shizuoka-ken (JP); Keiichiro Hayashi, Shizuoka-ken (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/887,335

(22) Filed: Jun. 25, 2001

(65) Prior Publication Data
US 2002/0033479 A1 Mar. 21, 2002

(30) Foreign Application Priority Data

Jun. 27, 2000 (JP) .......................... 2000-193142
Jun. 27, 2000 (JP) .......................... 2000-193143
Jan. 12, 2001 (JP) ............................ 2001-5740
Jan. 12, 2001 (JP) ............................ 2001-5741

(51) Int. Cl.[7] .................. C09K 19/52; C09K 19/34; C09K 19/32; C09K 19/38; G02F 1/13
(52) U.S. Cl. ..................... 252/299.01; 252/299.61; 252/299.62; 252/299.7; 428/1.1; 349/106; 349/2; 430/7; 430/19
(58) Field of Search .............. 252/299.61, 299.62, 252/299.01, 1.1; 428/1.1; 430/20, 7; 349/106, 2

(56) References Cited

U.S. PATENT DOCUMENTS 5,668,614 A   9/1997  Chien et al. ............... 349/115
6,217,792 B1 * 4/2001  Parri et al. ............. 252/299.61

FOREIGN PATENT DOCUMENTS

| JP | 11-248943 | 9/1999 | ............ G02B/5/30 |
| JP | 2000-44451 | 2/2000 | ............ A61K/7/42 |
| JP | 9-506088 | 6/2000 | ............ C07C/69/94 |
| WO | WO 95/16007 | 6/1995 | ............ C09K/19/34 |
| WO | WO 00/34808 | 6/2000 | ............ G02B/5/30 |

OTHER PUBLICATIONS

CAPLUS 2001: 783763.*

* cited by examiner

Primary Examiner—Shean C. Wu
(74) Attorney, Agent, or Firm—Sughrue Mion, PLLC

(57) ABSTRACT

A light-reaction type optically active compound and light-reaction type chiral agent of the following general formula (I) or (II). In the general formulae, $R^1$ and $R^2$ represent a hydrogen atom, an alkoxy group having 1 to 15 carbon atoms, an acryloyloxyalkyloxy group having 3 to 15 carbon atoms in total or a methacryloyloxyalkyloxy group having 4 to 15 carbon atoms in total.

General formula (I)

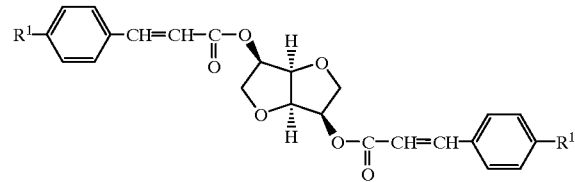

General formula (II)

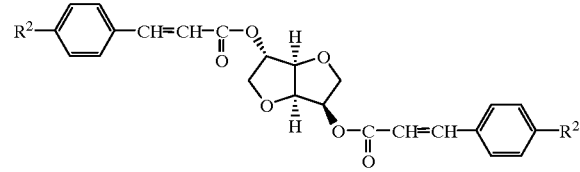

16 Claims, 3 Drawing Sheets

LIGHT-REACTION TYPE OPTICALLY ACTIVE COMPOUND, LIGHT-REACTION TYPE CHIRAL AGENT, LIQUID CRYSTAL COMPOSITION, LIQUID CRYSTAL COLOR FILTER, OPTICAL FILM, RECORDING MEDIUM, AND METHOD OF CHANGING TWIST STRUCTURE OF LIQUID CRYSTAL

BACKGROUND OF THE INVENTION

1. Field of the Invention

The present invention relates to a novel light-reaction type optically active compound, a light-reaction type chiral agent which changes the helical structure of a liquid crystal, a liquid crystal composition, an optical film, a liquid crystal color filter, a recording medium, and a method of changing the twist structure of helices of liquid crystals.

2. Description of the Related Art

Recently, liquid crystal materials such as cholesteric liquid crystals and the like having a helical structure and showing various selective reflected colors by twisting power (twist angle) of the helix have become prominent. Further, due to excellent selective reflecting property and excellent color purity of selective reflected light, the materials have become widely used in optical films, liquid crystal color filters, recording media and the like.

For example, a color filter used in a color liquid crystal display or the like is generally constituted of picture elements of red (R), green (G) and blue (B), and black matrices formed for the purpose of improving display contrast in gaps between the elements. Main types of such a color filter are conventionally those obtained by dispersing a pigment in a resin, or dyeing a resin with a dye. As a production method thereof, methods are usual in which a coloring resin solution is applied on a glass substrate by spin coating or the like to form a coloring resist layer, and patterning by a photolithography method is conducted to form color filter picture elements, or coloring picture elements are directly printed on a substrate.

However, for example, a production method by printing has problems in that resolution of picture elements is low and formation of an image pattern of high accuracy is difficult, and a production method by spin coating has problems in that material loss is large and application unevenness when applying on a substrate having large area is significant. Further, in a production method by electrodeposition, a color filter having relatively high resolution and having small unevenness of a colored layer can be obtained, but the production process is complicated and management of liquids is difficult.

As described above, there is a great desire for a method which can produce a color filter having high quality at high efficiency with small material loss and in a simple manner.

On the other hand, as characteristics of a color filter, high-percentage transmission and color purity are required. Recently, improvements corresponding to the above-mentioned requirements have been attempted by optimizing a dyeing resin and kind of dye in a method using a dye, and by using a more finely dispersed pigment in a method using a pigment. However, in recent liquid crystal display (LCD) panels, requirements for the percent transmission and color purity of a color filter are extremely high. Particularly in a color filter for a reflection type LCD, compatibility between white display of paper white, contrast and color reproducibility is difficult, while color filters produced by dyeing a resin with a dye or dispersing a pigment in a resin according to conventional production methods are all color filters of light absorption type. Therefore, improvement of color purity by a further increase in percent transmission is almost at an upper limit.

Against the above-mentioned situations, a color filter utilizing polarization, having a cholesteric liquid crystal as a main component, is known. This color filter utilizing polarization shows high efficiency of utilizing light and has more remarkable abilities also in percent transmission and color purity than a color filter of light absorption type, since a certain light amount is reflected and other light is transmitted to display images in the color filter utilizing polarization. On the other hand, as a method of producing the same filter, a method in which a film is formed on a substrate using a spin coat method or the like is usually conducted from the standpoint of uniform thickness. However, this method has a problem of large material loss and is disadvantageous in the point of cost.

As a means which can solve the above-mentioned problems, can secure uniformity of color purity and the like of a color filter film, and can also realize a reduction in the number of production steps, a method using a light-reaction type chiral compound is useful. This method uses the theory that when a liquid crystal composition containing a light-reaction type chiral compound is irradiated pattern-wise with light having a reaction wavelength of this chiral compound, the reaction of the chiral compound progresses depending on the strength of the irradiation energy, and helical pitch (twist angle of helix) of the liquid crystal compound changes. Consequently, a selective reflection color is formed for each picture element simply by pattern exposure including a difference between light amounts. Namely, there is a merit that patterning for forming a color filter can be completed by one-time mask exposure using a mask having different transmission light amounts.

Therefore, a film functioning as a color filter can be formed by effecting patterning by image-wise light irradiation, and then solidifying the patterned cholesteric liquid crystal compound. This can be applied also to films for optical use or recording of images, and the like.

Particularly when a color filter is produced by one-time mask exposure or the like, it is desired that three primary colors, B (blue), G (green) and R (red), can be formed with high color purity by one-time exposure. However, when a rate of change of twist of a liquid crystal is low, sufficient color purity is not obtained. Therefore, in view of displaying three primary colors having high color purity by one-time exposure, it is necessary to use a chiral compound (chiral agent) that is capable of changing twisting power of a helical structure of a liquid crystal compound and that has a high rate of change of twist as a light-reaction type chiral compound. Namely, a range of selectively reflected hues is enlarged due to change of light amount by using a chiral compound having a high rate of change of twist.

Further, Japanese Patent Application Laid-Open (JP-A) No. 11-248943 discloses use of a polymerizable mesogene compound having an isosorbide skeleton in a chiral mother nucleus as a chiral compound constituting a polarization plate of reflection type in a wide range. This polymerizable mesogene compound can act on a liquid crystal compound to cause change of the helical structure of the liquid crystal. However, when a reflection wavelength range of a polarization plate described in the above-mentioned publication is changed, namely, the helical structure (twisting power of helix) of a liquid crystal is changed so as to show the desired selective reflection, control of the change is carried out by a mixing ratio (of amounts used) of the mesogene compound to a non-chiral compound (liquid crystal), and light and light amount thereof are not correlated at all. That is, in this publication, there is utterly no suggestion that the helical structure (twisting power of helix) of a liquid crystal is changed by changing light amount, and there is also no suggestion that compounds exemplified in the publication are useful in the point of rate of change of twisting power in response to light.

As described above, a light-reaction type chiral agent as follows has not been proposed until now. This agent has light reactivity which can change orientation structures such as the helical pitch of a liquid crystal (twisting power, twist angle of helix) and the like by controlling light amounts used in irradiation. Further, in the case of a cholesteric liquid crystal phase containing a nematic liquid crystal compound, for example, the agent is able to provide significant changes of the helical pitch (twisting power), such as a wide range of selectively reflectable wavelengths, various selective reflections and, particularly, display of three primary colors (R, G, B) at high color purity, and the like.

SUMMARY OF THE INVENTION

An object of the present invention is to solve the above-mentioned various conventional problems and to attain the following objects.

Namely, a first object of the present invention is to provide a light-reaction type optically active compound which has light sensitivity and can be isomerized by light to reveal significant structural change. A second object of the present invention is to provide a light-reaction type chiral agent which can control the orientation of a liquid crystalline compound and manifests high rate of change of twisting power (twist angle, helical pitch) of a liquid crystal (hereinafter, sometimes referred to as twisting change rate) due to light, and in the case, for example, of a cholesteric liquid crystal phase, which can give selective reflection in a wide range containing three primary colors (B, G, R) and can display the three primary colors with high color purities.

A third object of the present invention is to provide a liquid crystal composition which contains a light-reaction type optically active compound or light-reaction type chiral agent that can change twisting power of a liquid crystal by light, and that has high twisting change rate, and which can change optical properties by sterically significantly controlling the orientation condition of a liquid crystal molecule by light, and in the case of, for example, a cholesteric liquid crystal, which shows selective reflection colors in a wide range containing three primary colors due to irradiation with light, and further, can display the three primary colors with excellent color purity.

Further, a fourth object of the present invention is to provide a liquid crystal color filter which contains a light-reaction type optically active compound or light-reaction type chiral agent that can significantly change twisting power of a liquid crystal when irradiated with light and has high color purity. A fifth object of the present invention is to provide an optical film which contains a light-reaction type optically active compound or light-reaction type chiral agent that can significantly change twisting power of a liquid crystal by irradiation with light, and in the case of, for example, a cholesteric liquid crystal phase, which manifests a wider selective reflection range and has high color purity. A sixth object of the present invention is to provide a recording medium which contains a light-reaction type optically active compound or light-reaction type chiral agent that can significantly change twisting power of a liquid crystal when irradiated with light, and that can form a bright image by image-wisely changing light amounts, and when, for example, the liquid crystal phase is a cholesteric liquid crystal phase, which can form images composed of selective reflection colors manifesting a wide hue range and having high color purity.

Further, a seventh object of the present invention is to provide a method of changing twist structure of a liquid crystal in which the twisting power (twist angle) of a liquid crystal can be changed significantly by irradiating with light a liquid crystal composition containing a light-reaction type optically active compound or light-reaction type chiral agent that reveals high twisting change rate.

A first aspect of the present invention is a light-reaction type optically active compound of the following general formula (I):

General formula (I)

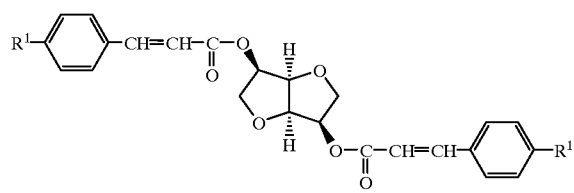

In the formula, $R^1$ represents a hydrogen atom, an alkoxy group having 1 to 15 carbon atoms, an acryloyloxyalkyloxy group having 3 to 15 carbon atoms in total or a methacryloyloxyalkyloxy group having 4 to 15 carbon atoms in total.

A second aspect of the present invention is a light-reaction type chiral agent which is composed of a compound of the general formula (I) or (II), and changes the twisting power of a liquid crystal by irradiation with light.

General formula (I)

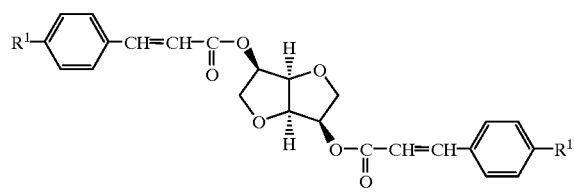

General formula (II)

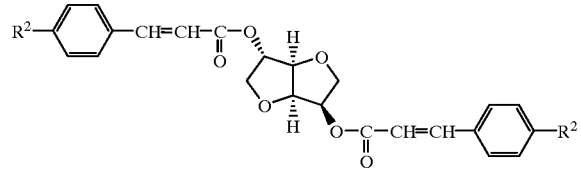

wherein, $R^1$ and $R^2$ represent a hydrogen atom, an alkoxy group having 1 to 15 carbon atoms, anacryloyloxyalkyloxy group having 3 to 15 carbon atoms in total or a methacryloyloxyalkyloxy group having 4 to 15 carbon atoms in total.

A third aspect of the present invention is a liquid crystal composition containing the above-mentioned light-reaction type optically active compound.

A fourth aspect of the present invention is a liquid crystal composition containing the above-mentioned light-reaction type chiral agent.

A fifth aspect of the present invention is a liquid crystal color filter containing the above-mentioned light-reaction type optically active compound.

A sixth aspect of the present invention is an optical film containing the above-mentioned light-reaction type optically active compound.

A seventh aspect of the present invention is a recording medium containing the above-mentioned light-reaction type optically active compound.

An eighth aspect of the present invention is a method of changing the twist structure of a liquid crystal including a step of irradiating the above-mentioned liquid crystal composition with light to cause a change of the twisting power of the liquid crystal.

A ninth aspect of the present invention is a liquid crystal color filter containing the above-mentioned light-reaction type chiral agent.

A tenth aspect of the present invention is an optical film containing the above-mentioned light-reaction type chiral agent.

An eleventh aspect of the present invention is a recording medium containing the above-mentioned light-reaction type chiral agent.

DETAILED DESCRIPTION OF THE PREFERRED EMBODIMENTS

Figure 1A:
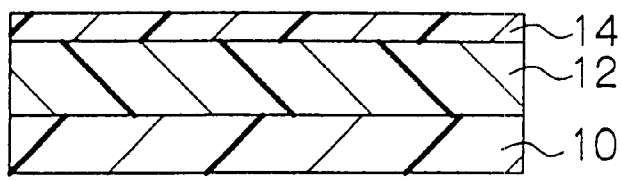
FIG. 1A is a sectional view showing a process of producing a liquid color filter of the present invention.

The present invention will be illustrated successively.
<Light-reaction Type Optically Active Compound>

The light-reaction type optically active compound of the present invention is a left-twisting compound of the following general formula (I).

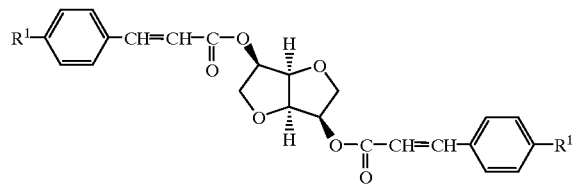

General formula (I)

In the formula, $R^1$ represents a hydrogen atom, an alkoxy group having 1 to 15 carbon atoms, an acryloyloxyalkyloxy group having 3 to 15 carbon atoms in total or a methacryloyloxyalkyloxy group having 4 to 15 carbon atoms in total.

Examples of the above-mentioned alkoxy group having 1 to 15 carbon atoms include a methoxy group, ethoxy group, propoxy group, butoxy group, hexyloxy group, octyloxy group, dodecyloxy group and the like, and, of these, alkoxy groups having 1 to 10 carbon atoms are preferable, and alkoxy groups having 1 to 8 carbon atoms are particularly preferable.

Examples of the above-mentioned acryloyloxyalkyloxy group having 3 to 15 carbon atoms in total include an acryloyloxy group, acryloyloxyethyloxy group, acryloyloxypropyloxy group, acryloyloxyhexyloxy group, acryloyloxybutyloxy group, acryloyloxydecyloxy group and the like, and, of these, acryloyloxyalkyloxy groups having 3 to 13 carbon atoms are preferable, and acryloyloxyalkyloxy groups having 3 to 11 carbon atoms are particularly preferable.

Examples of the above-mentioned methacryloyloxyalkyloxy group having 4 to 15 carbon atoms in total include a methacryloyloxy group, methacryloyloxyethyloxy group, methacryloyloxyhexyloxy group and the like, and, of these, methacryloyloxyalkyloxy groups having 4 to 14 carbon atoms are preferable, and methacryloyloxyalkyloxy groups having 4 to 12 carbon atoms are particularly preferable.

The molecular weight of a light-reaction type optically active compound of the above-mentioned general formula (I) is preferably 300 or more. Those showing high solubility with liquid crystalline compounds described below are preferable, and those having a solubility parameter SP value near those of the liquid crystalline compounds are more preferable.

Specific examples of a light-reaction type optically active compound of the above-mentioned general formula (I) include, but in the present invention are not limited to, the following compounds (exemplified compounds (1) to (12)).

(1)

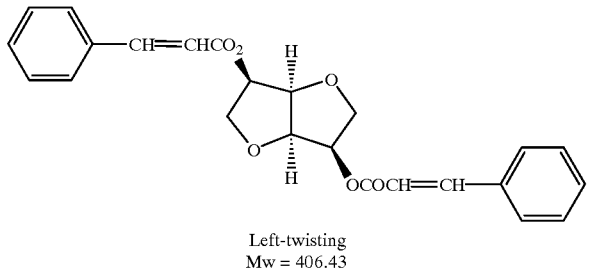

Left-twisting
Mw = 406.43

(2)

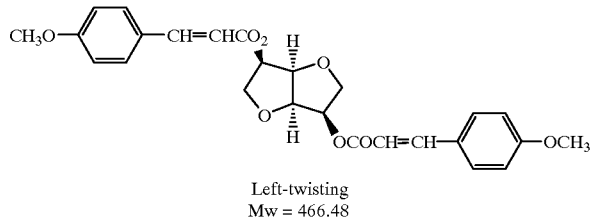

Left-twisting
Mw = 466.48

-continued
(3)
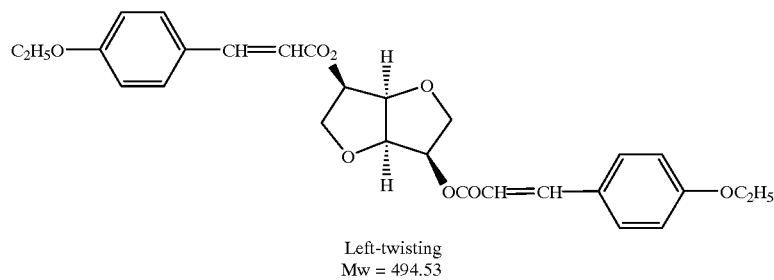
Left-twisting
Mw = 494.53
(4)
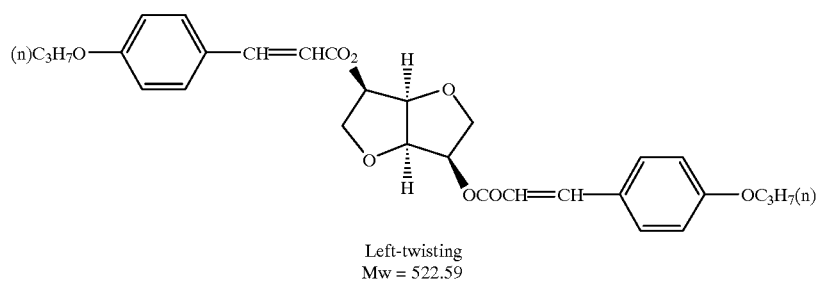
Left-twisting
Mw = 522.59
(5)
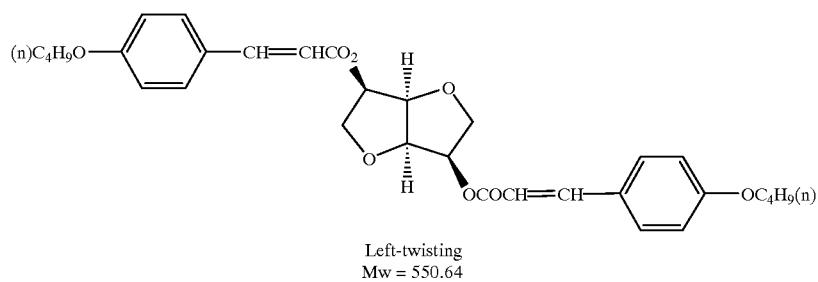
Left-twisting
Mw = 550.64
(6)
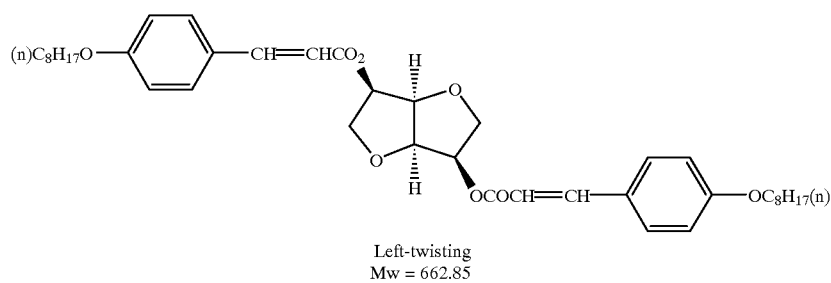
Left-twisting
Mw = 662.85
(7)
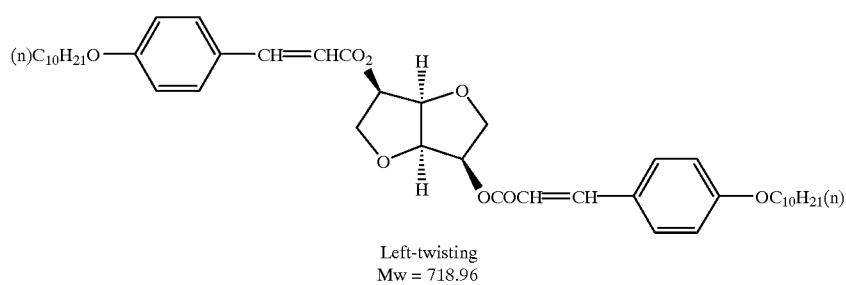
Left-twisting
Mw = 718.96

-continued

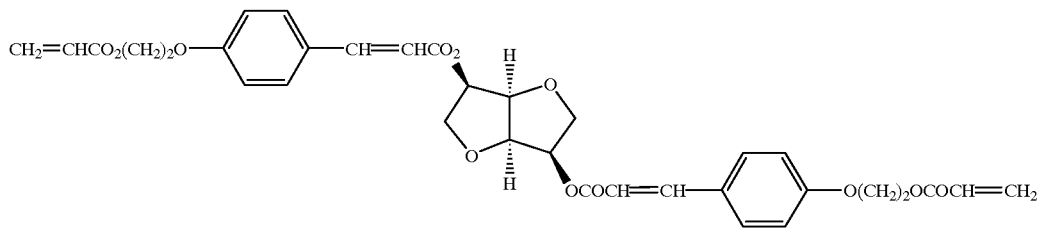

(8)

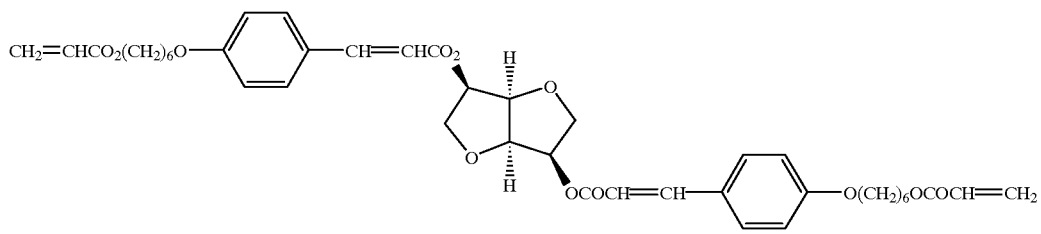

(9)

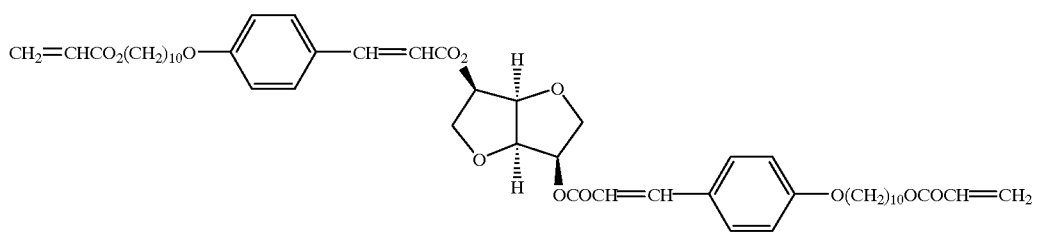

(10)

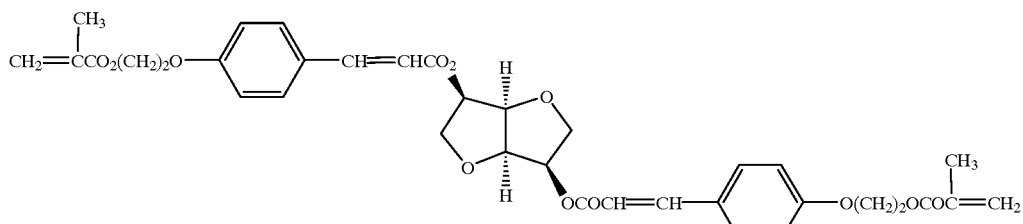

(11)

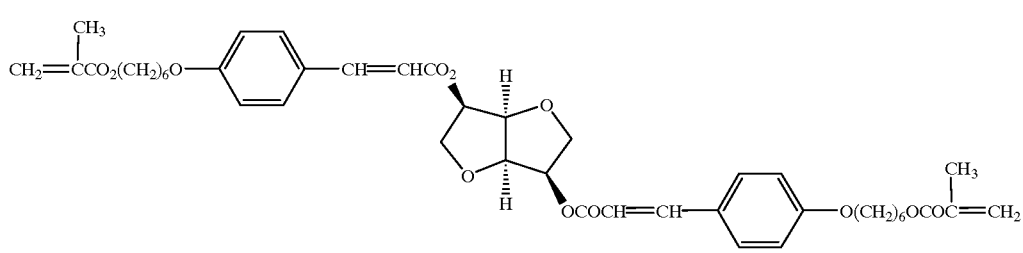

(12)

Next, examples of synthesizing light-reaction type optically active compounds of the present invention (compounds of the general formula (I)) will be described. A number in parentheses after a light-reaction type optically active ok compound represents the number of one of the above-exemplified light-reaction type optically active compounds (exemplified compounds).

[Synthesis of Light-reaction Type Optically Active Compound (2)]

4-methoxycinnamic acid (4 g, 0.022 mole) and dimethylformamide (2 to 3 drops) were dissolved in tetrahydrofuran (50 mL), and to this was further added dropwise a solution prepared by dissolving oxalyl chloride (10 mL, 0.034 mole) in tetrahydrofuran (20 mL), and these were reacted for 2 hours. The solvent and excess oxalyl chloride in the reaction solution were distilled off under reduced pressure. Then, the solution was diluted with tetrahydrofuran (30 mL), and to this was added isomannide (1.3 g, 0.009 mol). To this was further added dropwise triethylamine (18.6 mL, 0.13 mole) dissolved in tetrahydrofuran (20 mL) while stirring, and the mixture was stirred for 3 hours. Then, to the reaction solution was added 10% hydrochloric acid (50 mL) and ethyl acetate (100 mL) and this mixture was stirred, and separated. A resulting organic layer was washed once with saturated saline solution (50 mL), twice with saturated sodium bicarbonate solution (50 mL) and twice with saturated saline solution (50 mL) in this order, and dried over magnesium sulfate. Further, the organic solvent was distilled off under reduced pressure. Then, the solution was purified by silica gel column chromatography, using as a developing solvent a mixed solution of n-hexane-ethyl acetate (2:3 v/v), and re-crystallized (methanol-ethyl acetate) to obtain a pale yellow powdery crystal (4.1 g, 38%).

Identification results (data) of the pale yellow powdery crystal as obtained above are shown below.

Melting point Tm=132.5° C., $[\alpha]_D^{25} 407°$ (c0.10, EtOAc).
$^1$H-NMR (CDCl$_3$): δ (in ppm from tetramethylsilane) 7.70 (2H, d), 7.50 (4H, d), 6.90 (4H, d), 6.40 (2H, d), 5.30–5.20 (2H, m), 4.85–4.80 (2H, m), 4.15–3.90 (4H, m), 3.45 (6H, s).

[Synthesis of Light-reaction Type Optically Active Compound (7)]

Trans-4-courmaric acid (15 g, 0.091 mole) and potassium carbonate (30 g, 0.22 mole) were added todimethylformamide (100 mL), and to this mixture was added dropwise 1-iododecane (54 g, 0.21 mole) while heating in an oil bath. After stirring for 6 hours, insoluble components were filtrated off. The remaining solution was diluted with ethyl acetate (400 mL) and washed with saturated saline solution (200 mL). Further, the organic solvent was distilled off under reduced pressure. Then, to the remaining solution was added a solution prepared by dissolving ethanol (100 mL) and potassium hydroxide (10 g, 0,18 mole) in water (50 mL), and this mixture was refluxed for 1 hour. The reaction solution was poured into diluted hydrochloric acid, and deposited crystal was filtrated off before being dried to obtain 4-n-decyloxycinnamic acid (14.6 g, 53%) in the form of a colorless crystalline powder.

The resulting 4-n-decyloxycinnamic acid (3 g, 0.010 mole) and dimethylformamide (2 to 3 drops) were dissolved in tetrahydrofuran (50 mL). To this mixture was further added dropwise a solution prepared by dissolving oxalyl chloride (1.26 mL, 0.015 mole) in tetrahydrofuran (20 mL), and these were reacted for 2 hours. The solvent and excess oxalyl chloride in the reaction solution were distilled off under reduced pressure. Then, the solution was diluted with tetrahydrofuran (50 mL), and to this was added isomannide (0.6 g, 0.004 mol). To this was further added dropwise triethylamine (8.2 mL, 0.06 mole) dissolved in tetrahydrofuran (20 mL) while stirring, and this mixture was stirred for 3 hours. Then, to the reaction solution was added 10% hydrochloric acid (50 mL) and ethyl acetate (100 mL), and this mixture was stirred, and separated. A resulting organic layer was washed once with saturated saline solution (50 mL), twice with saturated sodium bicarbonate solution (50 mL) and twice with saturated saline solution (50 mL) in this order, and dried over magnesium sulfate. Further, the organic solvent was distilled off under reduced pressure, and then re-crystallized (n-hexane-ethyl acetate) to obtain a colorless powdery crystal (0.45 g, 16%).

Identification results (data) of the colorless crystalline powder as obtained above are shown below.

Melting point Tm=72.4° C., $[\alpha]_D^{25} 280°$ (c0.11, EtOAc).
$^1$H-NMR (CDCl$_3$): δ (in ppm from tetramethylsilane) 7.72 (2H, d), 7.48 (4H, d), 6.90 (4H, d), 6.38 (2H, d), 5.30–5.20 (2H, m), 4.85–4.78 (2H, m), 4.15–3.90 (8H, m), 1.90–1.30 (32H, m), 0.9 (6H, t).

<Light-reaction Type Chiral Agent>

The light-reaction type chiral agent is composed of a compound (light-reaction type optically active compound) of the general formula (I) or a compound of the general formula (II), and changes the twisting power of a crystal when irradiated with light.

A light-reaction type optically active compound of the above-mentioned general formula (I) has features that it functions, when used together with a crystalline compound, as a chiral compound (light-reaction type chiral agent) which changes the helical structure of the crystalline compound, and, when irradiated with light having a certain wavelength, the light-reaction type optically active compound having a sensitive wavelength at that wavelength range is sensitized, and this compound controls the orientation structure of the crystalline compound, and can simultaneously cause a change of the helical pitch of a crystal, namely, the twisting power of the helical structure (HTP: helical twisting power).

A light-reaction type chiral agent composed of a compound of the following general formula (II) also has features that it can control orientation structure of a crystalline compound and can cause change of the helical pitch, HTP, of the crystal when irradiated with light. That is, these light-reaction type chiral agents are compounds which cause, when irradiated with light (ultraviolet to visual to infrared), a change of the twisting power of a helical structure derived from a crystalline compound, preferably a nematic crystalline compound, and has a chiral site and a site causing a structural change by irradiation with light, as necessary sites (molecule structural units), in the same molecule.

Additionally, a light-reaction type chiral agent of the following general formula (I) or (II) can significantly change HTP of, particularly, a liquid crystal molecule. Consequently, for example, in the case of a cholesteric liquid crystal (liquid crystal phase) using a nematic liquid crystal compound as a crystalline compound, selective reflectances ranging over a wider wavelength range including three primary colors, B (blue), G (green) and R (red), can be obtained. The selective reflection property of light wavelength is determined by the twist angle of the helical structure of the liquid crystal molecule. When this angles varies more significantly, the width of colors selectively reflectable becomes wider, giving usefulness.

The above-described HTP represents the twisting power of the helical structure of a liquid crystal, namely, 1/(pitch× concentration of chiral agent [weight fraction])=HTP [$\mu m^{-1}$], and, for example, can be obtained by measuring the helical pitch (one cycle of helical structure; μm) of a liquid crystal molecule at a certain temperature, and converting this value using the concentration of the chiral agent.

When a selective reflection color is formed by the illuminance of light using the light-reaction type chiral agent, the above-mentioned change rate of HTP (=HTP before irradiation/HTP after irradiation) is preferably 1.5 or more, further preferably 2.5 or more if HTP becomes smaller after irradiation, and preferably 0.7 or less, further preferably 0.4 or less if HTP becomes larger after irradiation.

Next, compounds of the general formula (II) will be described.

General formula (II)

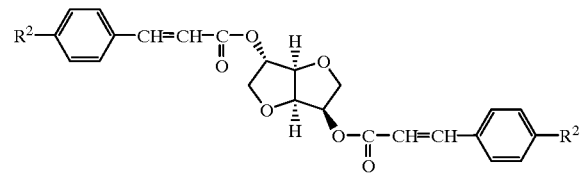

In the formula, $R^2$ represents a hydrogen atom, an alkoxy group having 1 to 15 carbon atoms, an acryloyloxyalkyloxy group having 3 to 15 carbon atoms in total or a methacryloyloxyalkyloxy group having 4 to 15 carbon atoms in total.

Examples of the above-mentioned alkoxy group having 1 to 15 carbon atoms include a methoxy group, ethoxy group, propoxy group, butoxy group, hexyloxy group, dodecyloxy group and the like, and, of these, alkoxy groups having 1 to 12 carbon atoms are preferable, and alkoxy groups having 1 to 8 carbon atoms are particularly preferable.

Examples of the above-mentioned acryloyloxyalkyloxy group having 3 to 15 carbon atoms in total include an acryloyloxyethyloxy group, acryloyloxybutyloxy group, acryloyloxydecyloxy group and the like, and, of these, acryloyloxyalkyloxy groups having 5 to 13 carbon atoms are preferable, and acryloyloxyalkyloxy groups having 5 to 11 carbon atoms are particularly preferable.

Examples of the above-mentioned methacryloyloxyalkyloxy group having 4 to 15 carbon atoms in total include a methacryloyloxyethyloxy group, methacryloyloxybutyloxy group, methacryloyloxydecyloxy group and the like, and, of these, methacryloyloxyalkyloxy groups having 6 to 14 carbon atoms are preferable, and methacryloyloxyalkyloxy groups having 6 to 12 carbon atoms are particularly preferable.

The molecular weight of a light-reaction type chiral agent of the above-mentioned general formula (II) is preferably 300 or more. Those showing high solubility with liquid crystalline compounds described below are preferable, and those having a solubility parameter SP value near that of the liquid crystalline compound are more preferable.

Specific examples of a compound of the above-mentioned general formula (II) include, but in the present invention are not limited to, the following compounds (exemplified compounds (13) to (27)).

(13)

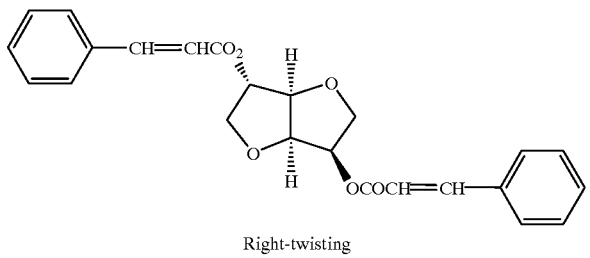

Right-twisting
Mw = 406.43

(14)

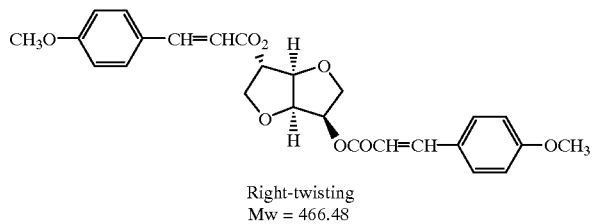

Right-twisting
Mw = 466.48

(15)

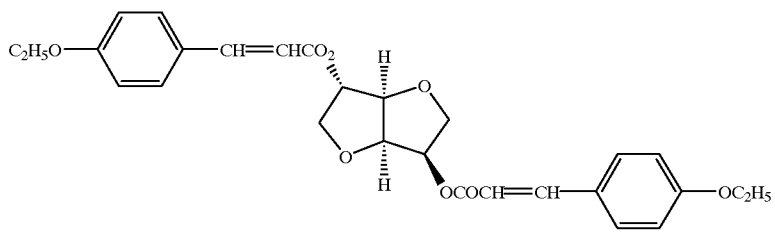

Right-twisting
Mw = 494.53

(16)

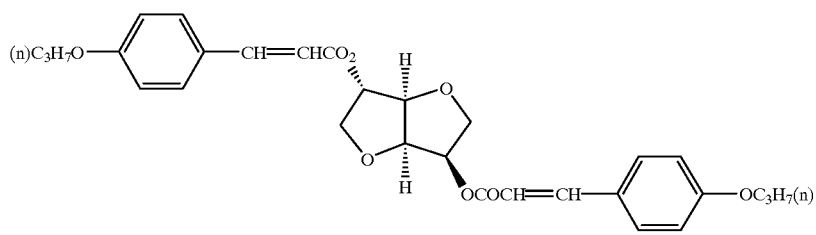

Right-twisting
Mw = 522.59

(17)

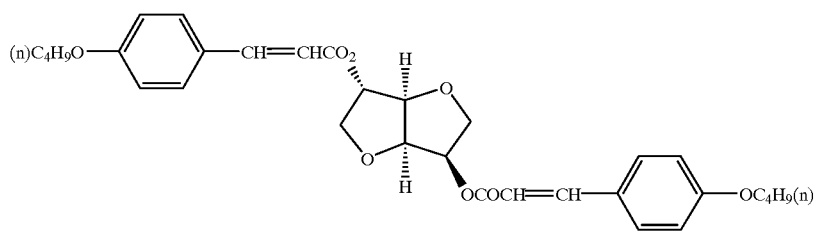

Right-twisting
Mw = 550.64

-continued
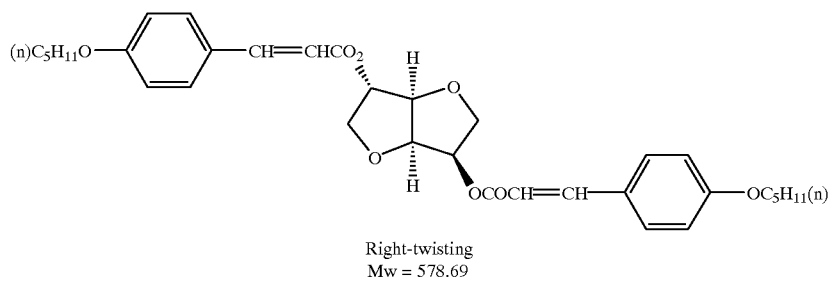
(18)
Right-twisting
Mw = 578.69
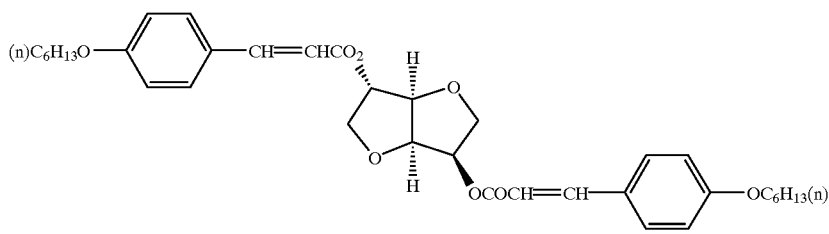
(19)
Right-twisting
Mw = 606.75
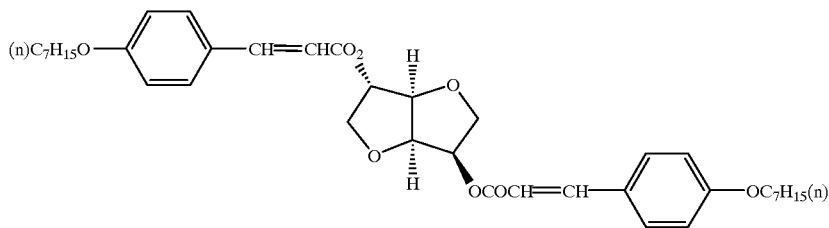
(20)
Right-twisting
Mw = 634.80
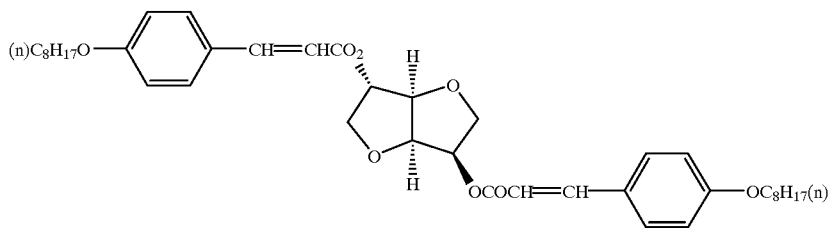
(21)
Right-twisting
Mw = 662.85
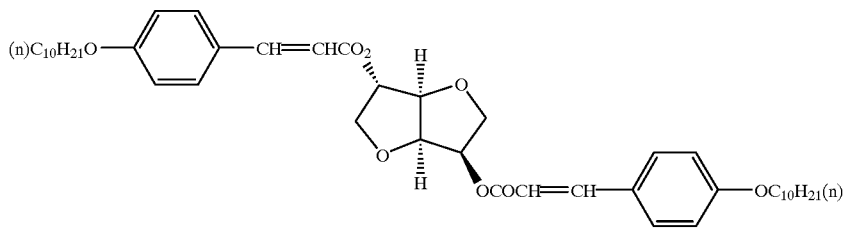
(22)
Right-twisting
Mw = 718.96

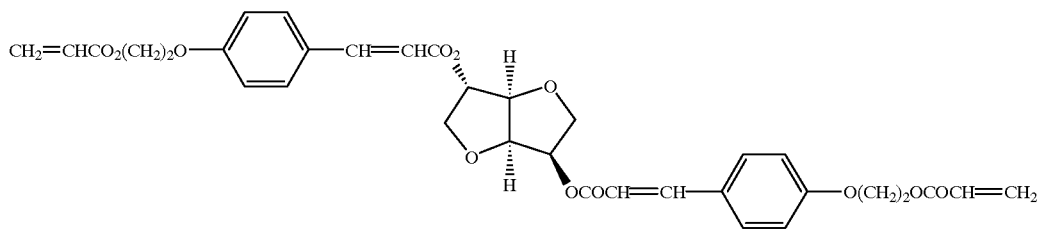

(23)

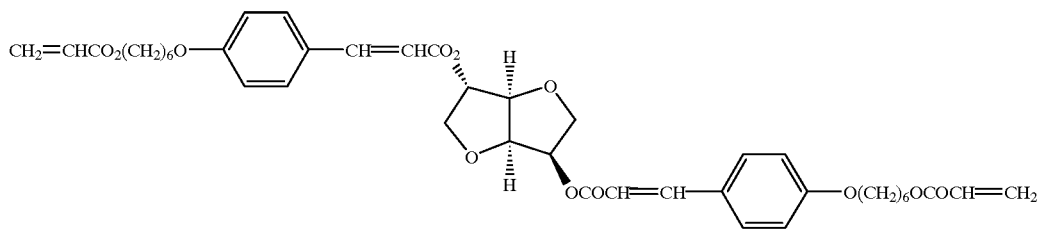

(24)

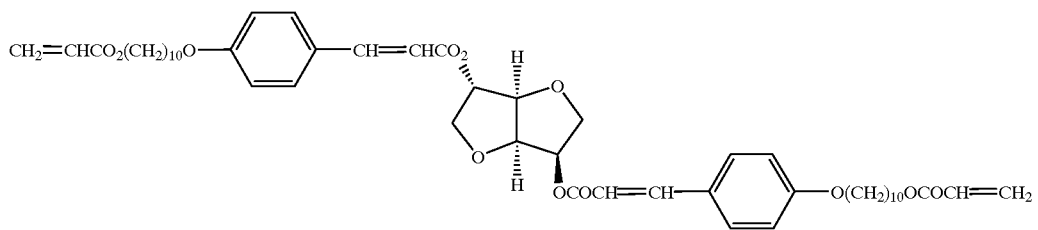

(25)

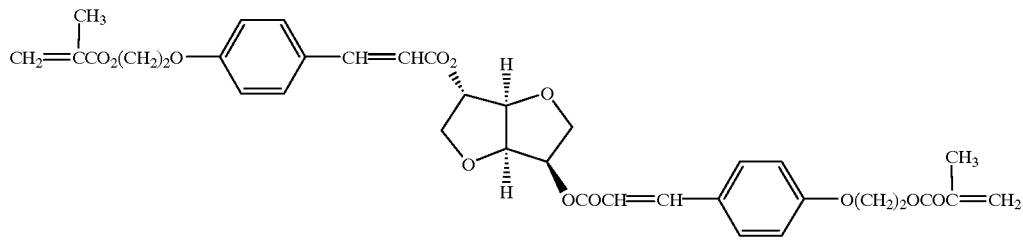

(26)

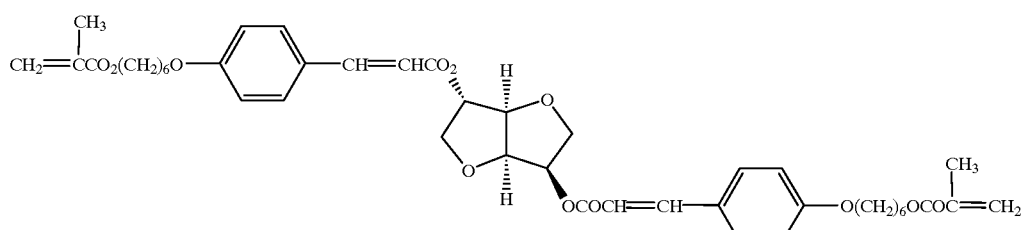

(27)

Next, examples of synthesizing compounds of the general formula (II) will be described. A number in parentheses after a light-reaction type chiral agent represents the number of one of the above exemplified light-reaction type chiral agents (exemplified compounds).

[Synthesis of Light-reaction Type Chiral Agent (14)]

4-methoxycinnamic acid (15 g, 0.084 mole) and dimethylformamide (2 to 3 drops) were dissolved in tetrahydrofuran (100 mL), and to this was further added dropwise a solution prepared by dissolving oxalyl chloride (10 mL, 0.13 mole) in tetrahydrofuran (50 mL), and they were reacted for 2 hours. The solvent and excess oxalyl chloride in the reaction solution were distilled off under reduced pressure. Then, the solution was diluted with tetrahydrofuran (100 mL), and to this was added isosorbide (5.5 g, 0.038 mole). To this was further added dropwise pyridine (27 mL, 0.33 mole) dissolved in tetrahydrofuran (50 mL) while stirring, and the mixture was stirred for 3 hours. Then, to the reaction solution was added 10% hydrochloric acid (100 mL) and ethyl acetate (200 mL) and this mixture was stirred, and separated. A resulting organic layer was washed once with saturated saline solution (100 mL), twice with saturated sodium bicarbonate solution (100 mL) and twice with saturated saline solution (100 mL) in this order, and dried over magnesium sulfate. Further, the organic solvent was distilled off under reduced pressure. Then, the solution was purified by silica gel column chromatography using as a developing solvent a mixed solution of n-hexane-ethyl acetate (3:2 v/v), and re-crystallized (n-hexane-ethyl acetate) to obtain a colorless crystal (9.8 g, 56%).

Identification results (data) of the colorless crystal as obtained above are shown below.

Melting point Tm=113.7° C., $[\alpha]_D^{25}$-158° (c0.50, EtOAc).

$^1$H-NMR (CDCl$_3$) δ (in ppm from tetramethylsilane) 7.75–7.60 (2H, dd), 7.50–7.45 (4H, dd), 6.94–6.88 (4H, dd), 6.40–6.25 (2H, dd), 5.36–5.26 (2H, m), 4.95 (1H, t), 4.60 (1H, d), 4.15–3.90 (8H, m), 3.85 (6H, s).

[Synthesis of Light-reaction Type Chiral Agent (17)]

Trans-4-courmaric acid (20 g, 0.12 mole) and potassium carbonate (33 g, 0.24 mole) were dispersed in dimethylformamide (100 mL), and to this mixture was added dropwise n-bromobutane (50 g, 0.37 mole) while heating in an oil bath. After stirring for 3 hours, insoluble components were filtrated off, and the remaining solution was diluted with ethyl acetate (400 mL) and washed with saturated saline solution (200 mL). Further, the organic solvent was distilled off under reduced pressure. Then, to the remaining solution was added a solution prepared by dissolving ethanol (100 mL) and potassium hydroxide (20 g, 0,36 mole) in water (50 mL), and the mixture was refluxed for 1 hour. The reaction solution was poured into diluted hydrochloric acid, and deposited crystal was filtrated off and dissolved in chloroform (500 mL). A resulting organic layer was washed with saturated saline solution, and dried over magnesium sulfate. Further, the organic solvent was distilled off under reduced pressure, and then recrystallized (n-hexane-ethyl acetate) to obtain 4-n-butoxycinnamic acid (22.7 g, 84%) in the form of a colorless crystal.

The resulting 4-n-butoxycinnamic acid (5 g, 0.023 mole) and dimethylformamide (2 to 3 drops) were dissolved in tetrahydrofuran (50 mL), and to this mixture was further added dropwise a solution prepared by dissolving oxalyl chloride (2.9 mL, 0.034 mole) in tetrahydrofuran (30 mL). These were reacted for 2 hours. The solvent and excess oxalyl chloride in the reaction solution were distilled off under reduced pressure. Then, the solution was diluted with tetrahydrofuran (50 mL), and to this was added isosorbide (1.5 g, 0.010 mol). To this was further added dropwise pyridine (11 mL, 0.14 mole) dissolved in tetrahydrofuran (20 mL) while stirring, and the mixture was stirred for 3 hours. Then, to the reaction solution was added 10% hydrochloric acid (50 mL) and ethyl acetate (100 mL) and this mixture was stirred, and separated. A resulting organic layer was washed once with saturated saline solution (50 mL) twice with saturated sodium bicarbonate solution (50 mL) and twice with saturated saline solution (50 mL) in this order, and dried over magnesium sulfate. Further, the organic solvent was distilled off under reduced pressure, then purified by silica gel column chromatography, using as a developing solvent a mixed solution of n-hexane-ethyl acetate (2:1 v/v), and re-crystallized (n-hexane-ethyl acetate) to obtain a colorless crystalline powder (1.4 g, 25%).

Identification results (data) of the colorless crystalline powder as obtained above are shown below.

Melting point Tm=132.4° C., $[\alpha]_D^{25}$-115.0° (c0.10, EtOAc).

$^1$H-NMR (CDCl$_3$): δ (in ppm from tetramethylsilane) 7.75–7.65 (2H, dd), 7.50–7.45 (4H, dd), 6.90–6.85 (4H, dd), 6.40–6.26 (2H, dd), 5.35–5.25 (2H, m), 4.94 (1H, t), 4.60 (1H, d), 4.13–3.95 (8H, m), 1.94–1.65 (4H, m), 1.55–1.44 (4H, m), 0.95 (6H, t).

[Synthesis of Light-reaction Type Chiral Agent (24)]

Trans-4-courmaric acid (20 g, 0.12 mole), potassium iodide (24 g, 0.14 mole) and potassium carbonate (85 g, 0.62 mole) were dispersed in dimethylformamide (200 mL) and water (100 mL), and to this mixture was added dropwise 6-chlorohexanol (68 g, 0.50 mole) while heating in an oil bath. After stirring for 3 hours, the solution was diluted with ethyl acetate (400 mL) and washed with saturated saline solution (400 mL). Further, the organic solvent was distilled off under reduced pressure. Then, to the remaining solution was added a solution prepared by dissolving ethanol (200 mL) and potassium hydroxide (20 g, 0,36 mole) in water (50 mL), and this mixture was refluxed for 1 hour. The reaction solution was poured into diluted hydrochloric acid, and deposited crystal was filtrated off and then dried to obtain 4-(6-hydroxyhexyloxy)cinnamic acid (22 g, 64%) in the form of a colorless crystalline powder.

The resulting 4-(6-hydroxyhexyloxy)cinnamic acid (6 g, 0.023 mole) and N,N-dimethylaniline (6.6 g, 0.054 mole) were dissolved in tetrahydrofuran (50 mL), and to this mixture was further added dropwise a solution prepared by dissolving acryloyl chloride (4.4 g, 0.049 mole) in tetrahydrofuran (20 mL). After this addition, the mixture was stirred for 4 hours. Then, the reaction solution was poured into 10% hydrochloric acid, and deposited crystal was filtrated off. The resulting coarse crystal was dissolved in ethyl acetate (100 mL), and an organic layer was washed with saturated saline solution and dried over magnesium sulfate. The organic solvent was distilled off under reduced pressure, and then the coarse crystal was re-crystallized (n-hexane-ethyl acetate) to obtain 4-(6-acryloyloxyhexyloxy)cinnamic acid (3.9 g, 54%) in the form of a colorless crystalline powder.

The resulting 4-(6-acryloyloxyhexyloxy)cinnamic acid (3 g, 9.4 mole) and dimethylformamide (2 to 3 drops) were dissolved in tetrahydrofuran (50 mL), and to this mixture was further added dropwise a solution prepared by dissolving oxalyl chloride (1.2 mL, 0.014 mole) in tetrahydrofuran (10 mL), and these were reacted for 2 hours. The solvent and excess oxalyl chloride in the reaction solution were distilled off under reduced pressure. Then, the solution was diluted with tetrahydrofuran (50 mL), and to this was added isosorbide (0.6 g, 4.1 mmole). To this was further added dropwise pyridine (4.5 mL, 0.056 mole) dissolved in tetrahydrofuran (20 mL) while stirring, and the mixture was stirred overnight. Then, to the reaction solution was added 10% hydrochloric acid (50 mL) and ethyl acetate (100 mL), and the mixture was stirred, and separated. A resulting organic layer was washed once with saturated saline solution (50 mL), twice with saturated sodium bicarbonate solution (50 mL) and twice with saturated saline solution (50 mL) in this order, and dried over magnesium sulfate. The organic solvent was distilled off under reduced pressure, and then purified by silica gel column chromatography, using as a developing solvent a mixed solution of n-hexane-ethyl acetate (3:2 v/v), to obtain a colorless crystalline powder (1.1 g, 38%).

Identification results (data) of the colorless crystalline powder as obtained above are shown below.

Melting point Tm=70.5° C., $[\alpha]_D^{25}$-103.0° (c0.11, EtOAc).

$^1$H-NMR (CDCl$_3$): δ (in ppm from tetramethylsilane) 7.75–7.65 (2H, dd), 7.50–7.45 (4H, dd), 6.92–6.88 (4H, dd), 6.45–5.88 (8H, m), 5.35–5.25 (2H, m), 4.95 (1H, t), 4.60 (1H, d), 4.20–3.85 (8H, m), 1.94–1.65 (4H, m), 1.85–1.45 (16H, m).

A light-reaction type chiral agent of the above-mentioned general formula (I) or (II) can cause a significant change of the twisting power of the helical structure of a crystal. Further, in the case of a structure in which one or more polymerizable bonding groups have been introduced in the structure, the light-reaction type chiral agent of the present invention can improve heat resistance of a liquid crystal composition, a liquid crystal color filter or an optical film containing a liquid crystal composition.

Further, the light-reaction type chiral agent of the present invention can also be used together with a chiral agent having no light reactivity, such as a chiral compound showing high dependency of twisting power on temperature, or the like. The above-mentioned known chiral agent having no light reactivity includes chiral agents described, for example, in JP-A Nos. 2000-44451, 10-509726, WO98/00428, JP-A Nos. 2000-506873 and 9-506088, "Liquid Crystals" (1996, 21, 327), "Liquid Crystals" (1998, 24, 219) and the like.

<Liquid Crystal Composition>

A liquid crystal composition contains at least one selected from the above-mentioned light-reaction type chiral agents of the present invention or a light-reaction type optically active compound of the general formula (I). Embodiments further containing at least one liquid crystalline compound (preferably, a nematic liquid crystal compound) are preferable, and the above-mentioned liquid crystalline compound may have a polymerizable group or may not have a polymerizable group. Further, if necessary, other components such as a polymerizable monomer, polymerization initiator, binder resin, solvent, surfactant, polymerization inhibitor, thickening agent, coloring matter, pigment, ultraviolet absorber, gelling agent and the like may also be contained.

In the liquid crystal composition of the present invention, particularly, it is preferable to also use a surfactant. For example, an orientation condition at an air interface at the surface of a layer can be sterically controlled and a selective reflection wavelength having higher color purity can be obtained, such as in cases of application of a liquid crystal composition in the form of a coating solution to form a layer.

(Light-reaction Type Chiral Agent)

The liquid crystal composition of the present invention contains as the light-reaction type chiral agent the above-mentioned light-reaction type chiral agent of the present invention or a light-reaction type optically active compound of the general formula (I), and sterically controls the orientation structure of the liquid crystal molecules and the helical structure of a liquid crystalline compound therewith, which is preferably a nematic liquid crystal compound, is changed by effecting light irradiation in desired patterns and light amounts. In a system containing a nematic liquid crystal compound, selective reflection colors in a wide wavelength range can be manifested.

The content of the light-reaction type chiral agent in the liquid crystal composition is not particularly restricted and can be appropriately selected, and is preferably from about 2 to 30% by weight.

(Liquid Crystalline Compound)

The liquid crystalline compound can be appropriately selected from liquid crystal compounds having a refractive index anisotropy An of 0.10 to 0.40, polymer liquid crystal compounds, and polymerizable liquid crystal compounds. For example, smectic liquid crystal compounds and nematic liquid crystal compounds and the like are listed, and among them, nematic liquid crystal compounds are preferable. For example, a cholesteric liquid crystal composition (cholesteric liquid crystal phase) can be obtained by using a nematic liquid crystal compound as a liquid crystalline compound, and using a light-reaction type chiral agent of the above-mentioned general formula (I) or (II) together therewith.

The above-mentioned liquid crystalline compound can be oriented, when it is in the liquid crystal condition of melting, by using an oriented substrate on which orientation treatments such as a rubbing treatment and the like have been performed for example. Further, when liquid crystal condition is converted into solid phase for fixing, a means such as cooling, polymerization or the like can be used.

As specific examples of the above-mentioned liquid crystalline compound, the following compounds are listed. However, they do not limit the scope of the present invention.

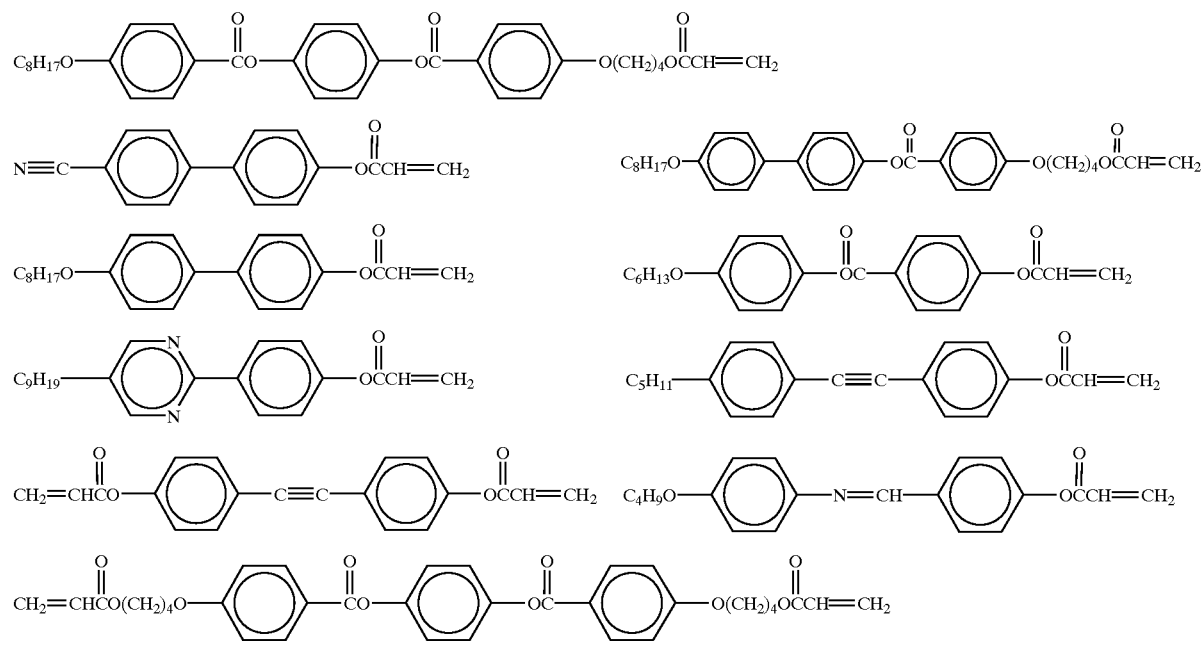

-continued

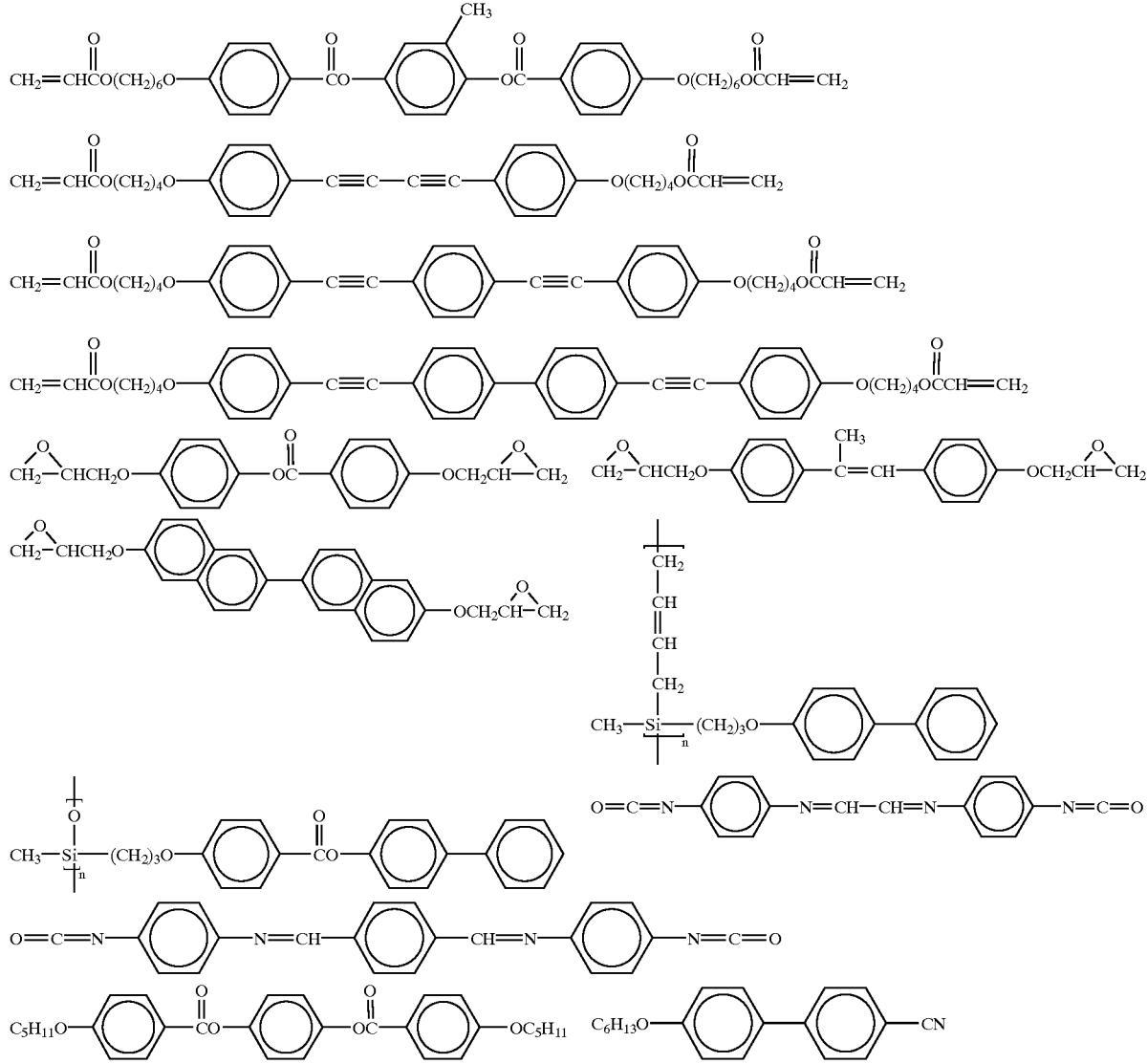

In the above-mentioned formulae, n represents an integer from 1 to 1000.

In the above-mentioned exemplified compounds, those in which a connecting group on an aromatic ring has been converted into one of the following structures may be listed as suitable examples.

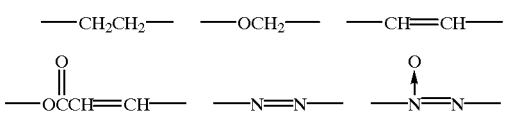

Among the above-mentioned compounds, liquid crystalline compounds having a polymerizable group or cross-linkable group in the molecule are preferable from the standpoint of securing of sufficient hardening property and giving heat resistance of a layer.

The content of the above-mentioned liquid crystalline compound is preferably from 30 to 99.9% by weight, more preferably from 50 to 95% by weight based on the total solid content (by weight) of a liquid crystal composition. When the above-mentioned content is less than 30% by weight, orientation may be insufficient, and particularly in the case of a cholesteric liquid crystal, desired selective reflection colors may not be obtained.

(Polymerizable Monomer)

The liquid crystal composition of the present invention may contain a polymerizable monomer therein, for the purpose of improving extent of hardening, such as film strength or the like. When the polymerizable monomer is used, it is possible that after the twisting power of a liquid crystal has been changed (patterning) by light irradiation (for example, after formation of a distribution of selective reflection wavelengths), then the helical structure thereof (selective reflection property) is fixed, and the strength of the liquid crystal composition after fixing can be improved. However, when the above-mentioned liquid crystalline compound has an unsaturated bond in the same molecule, this addition is not necessarily required.

The above-mentioned polymerizable monomer includes, for example, monomers having an ethylenically unsaturated bond, and the like, and specifically includes poly-functional monomers such as pentaerythritol tetraacrylate, dipentaerythritol hexaacrylate and the like.

Specific examples of the above-mentioned monomers having an ethylenically unsaturated bond include, but in the present invention are not limited to, the following compounds.

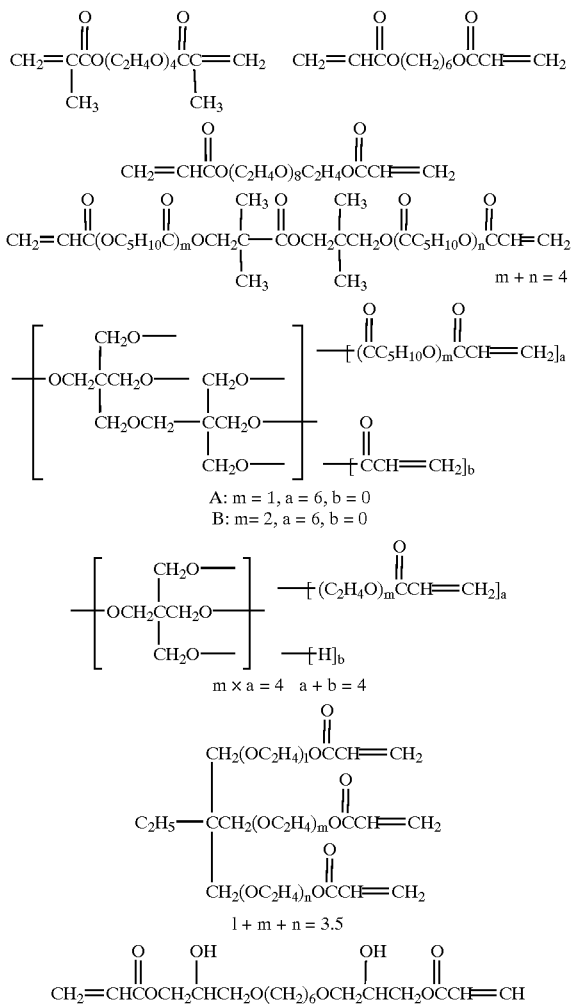

The amount of the above-mentioned polymerizable monomer added is preferably from 0.5 to 50% by weight based on the total solid content (by weight) of the liquid crystal composition. If the addition amount is less than 0.5% by weight, sufficient hardening property may not be obtained, and if over 50% by weight, the orientation of liquid crystal molecules will be disturbed and sufficient color development may not be obtained.

(Photopolymerization Initiator)

The liquid crystal composition of the present invention may also contain a photopolymerization initiator and, by simultaneous use of this photopolymerization initiator, it is possible that a polymerization reaction of a polymerizable group will be promoted, helical structure after helical pitch (twisting power) of the liquid crystals has been changed by light irradiation will be fixed, and the strength of the liquid crystal composition after fixing will be improved. If a polymerization reaction using a polymerizable crystalline compound is to be utilized for fixation of the helical structure of the liquid crystal, the photopolymerization initiator is preferably added.

For example, if the liquid crystal phase is a cholesteric liquid crystal phase, desired helical pitch can be obtained stably, and selective reflection colors having high color purity can be secured.

The above-mentioned photopolymerization initiator can be appropriately selected from known compounds, and examples thereof include p-methoxyphenyl-2,4-bis (trichloromethyl)-s-triazine, 2-(p-butoxystyryl)-5-trichloromethyl-1,3,4-oxadiazole, 9-phenylacridine, 9,10-dimethylbenzphenazine, benzophenone/Michler's ketone, hexaarylbiimidazole/mercaptobenzimidazole, benzyldimethylketal, thioxanthone/amine, triarylsulfonium-hexafluorophosphate and the like, bisacylphosphine oxides described in JP-A No. 10–29997 such as bis(2,4,6-trimethylbenzoyl)-phenylphosphine oxide and the like, acylphosphine oxides described in DE4230555 and the like, of Lucirin TPO and the like, and the like.

The amount of the above-mentioned photopolymerization initiator added is preferably from 0.1 to 20% by weight, more preferably from 0.5 to 5% by weight based on the total solid content (by weight) of the liquid crystal composition. If the addition amount is less than 0.1% by weight, a longer period of time may be necessary due to low hardening efficiency in light irradiation, and if over 20% by weight, light percent transmission may be inferior from the ultraviolet region the to visible region.

(Other Components)

Further, as other components, a binder resin, solvent, surfactant, polymerization inhibitor, thickening agent, coloring matter, pigment, ultraviolet absorber, gelling agent and the like can also be added.

The above-mentioned binder resin includes, for example, polystyrene compounds such as polystyrene, poly-α-methylstyrene and the like, cellulose resins such as methylcellulose, ethylcellulose, acetylcellulose and the like, acidic cellulose derivatives having a carboxyl group on a side chain, acetal resins such as polyvinylformal, polyvinylbutyral and the like, and methacrylic acid copolymers, acrylic acid copolymers, itaconic acid copolymers, crotonic acid copolymers, maleic acid copolymers, partially-esterified maleic acid copolymers and the like described in JP-A No. 59–44615, JP-B Nos. 54–34327, 58–12577 and 54–25957, JP-A Nos. 59–53836 and 59–71048.

Homopolymers of alkyl acrylates and homopolymers of alkyl methacrylates are also listed, and, as examples thereof, those in which the alkyl group is a methyl group, ethyl group, n-propyl group, n-butyl group, iso-butyl group, n-hexyl group, cyclohexyl group, 2-ethylhexyl group or the like are listed.

In addition, those obtained by adding an acid anhydride to a polymer having a hydroxyl group, and a benzyl (meth) acrylate/(meth)acrylic acid copolymer, multiple copolymers of benzyl (meth)acrylate/(meth) acrylic acid/other monomers, and the like, are listed.

The content of the binder resin in the liquid crystal composition is preferably from 0 to 50% by weight, more preferably from 0 to 30% by weight. If the above-mentioned content is over 50% by weight, the orientation of the liquid crystalline compound may be insufficient.

In the liquid crystal composition of the present invention, it is preferable to use a surfactant together with a light-reaction type chiral agent and a liquid crystalline compound from the standpoint of more improvement of color purity of a hue that is selectively reflected. As the surfactant, surfactants exerting an exclusion volume effect are preferable. Here, exertion of an exclusion volume effect means that when a layer containing a liquid crystal composition is formed by application, a spatial orientation condition at the air interface on the layer surface is sterically controlled.

Specifically, nonionic surfactants are preferable, and surfactants appropriately selected from know nonionic surfactants can be used.

The above-mentioned polymerization inhibitor can be added for the purpose of improving storability. For example, hydroquinone, hydroquinone monomethyl ether, phenothiazine, benzoquinone and derivatives thereof are listed. The amount of the polymerization inhibitor added is preferably from 0 to 10% by weight, and more preferably from 0 to 5% by weight based on the above-mentioned polymerizable monomer.

The liquid crystal composition of the present invention can be prepared by dissolving or dispersing components in a suitable solvent, and can be molded into any form or formed on a supporting substrate or the like. As the above-mentioned solvent, for example, 2-butanone, cyclohexanone, methylene chloride, chloroform and the like are listed.

<Method of Changing Twist Structure of Liquid Crystal>

As described above, the liquid crystal composition of the present invention contains a light-reaction type chiral agent or a light-reaction type optically active compound, and, in the method of changing the twist structure of the liquid crystal of the present invention, the above-mentioned liquid crystal composition of the present invention is irradiated with light while changing light amounts to cause a change of twisting power of the liquid crystal and to form regions having different twist structure of the liquid crystals. That is, by irradiating the liquid crystal composition with light using desired light amounts in desired patterns, the twist structure of the liquid crystal, namely, extent of twisting of helices (twisting power; HTP) can be changed, and selective reflection colors manifested by the liquid crystal depending on the twisting power can be changed optionally.

Particularly, when the liquid crystal phase is a cholesteric liquid crystal phase, selective reflection colors manifested by the liquid crystals depending on twisting power can be changed optionally. When change rate of this twisting power is large, color width of selective reflection colors which can be selectively reflected by the liquid crystal is wide, and selective reflection in a wide wavelength range including three primary colors (B, G, R) can be obtained. This is particularly important in that the three primary colors RGB can be displayed with high color purity. In this point, particularly the above-mentioned light-reaction type optically active compound and light-reaction type chiral agent of the general formula (I) or (II) can significantly change the twisting power of the helical structure of the liquid crystals. Consequently, by use of a liquid crystal composition containing this compound and/or chiral agent, hues in a wide range including blue (B), green (G) and red (R) can be displayed, and three primary colors having excellent color purities can be obtained.

Specific procedures are described below.

When a liquid crystal composition is irradiated with light having a certain wavelength, a light-reaction type chiral agent or light-reaction type optically active compound therewith causes a change of the helical structure (twist angle) of a liquid crystal based on irradiation strength. By this structural change, different selective reflection colors are displayed and image-wise patterns are formed (patterning). In the case of a cholesteric liquid crystal composition, different selective reflection colors are shown by this structural change. Accordingly, light irradiation is effected using irradiation strength changed for each desired range, orientation is effected (a plurality of colors are displayed) corresponding to irradiation strength, and, for example, by conducting exposure via a mask for exposure made with light percent transmissions varied image-wise, images can be formed by one-time light irradiation. That is, colored regions having different selective reflections can be formed simultaneously.

Further, a compound of the general formula (I) or (II) can significantly change the helical pitch of the liquid crystals, and in the case of a cholesteric liquid crystal composition, colored regions that are formed show a wide range of selective reflection colors, and three primary colors BGR, which are excellent in color purity, can be formed. This light irradiation can be conducted without specific limitation by methods which can change irradiation strength at each desired region, in addition to the method using a mask for exposure.

When a liquid crystal color filter and an optical film and the like described later are formed, exposure is effected image-wise with light having a certain wavelength as described above to cause patterning. Then, light irradiation is further conducted to cause photopolymerization of a polymerizable group in a liquid crystal composition to harden the composition, and the helical structures of liquid crystals are fixed at desired selective reflection colors. Details of this formation method are described later.

As the light source used for light irradiation, light sources emitting ultraviolet radiation are preferable since they have high energy, and structural change and polymerization of a liquid crystal compound can be effected quickly. For example, a high pressure mercury lamp, metal halide lamp, Hg—Xe lamp and the like are listed. Further, it is preferable that the light source has a function which can change light amount.

As described above, by use of a light-reaction type optically active compound or a light-reaction type chiral agent of the general formula (I) or (II), the twisting power of the helical structure of a liquid crystal depending on light amount can be significantly changed. Therefore, for example, in the case of a cholesteric liquid crystal phase using a nematic liquid crystal composition as the liquid crystalline compound, the color width of selective reflection colors which can be manifested by the liquid crystal is enlarged, and three primary colors, blue (B), green (G) and red (R), excellent in color purity can be obtained.

By utilizing the large change rate of helical pitch caused in the liquid crystal phase by light irradiation because of the light-reaction type optically active compound or light-reaction type chiral agent of the above-mentioned general formula (I) or (II), liquid color filters, and circular polarization separation films, glasses for stereoscopic vision, polarization masks and the like, which are used as optical films can be formed as described later. Further, this can be applied also to wide-region switchable mirrors, recording media of light-recording types, and the like. Patterning of polarization conditions and patterning of helical pitch by doping the liquid crystal composition of the present invention into a ferroelectric liquid crystal, antiferroelectric liquid crystal or TGB phase become possible. Further, use as a usual optical active compound is of course possible, and application to a helical structure-inducing agent for STN elements and TN elements is also possible.

In the liquid crystal composition of the present invention, non-chiral azo-based or styrene-based compounds which are isomerized by light can also be compounded, and change rate of helical pitch by light irradiation may be further increased in some cases.

A liquid crystal color filter, optical film and recording medium will be illustrated in detail below.

<Liquid Crystal Color Filter>

The liquid crystal color filter of the present invention contains at least one selected from the above-mentioned light-reaction type optically active compound or light-reaction type chiral agents of the present invention, further, embodiments containing at least one liquid crystalline compound are preferable, and, as this liquid crystalline compound, a nematic liquid crystal compound is most preferable. Further, if necessary, other components listed for the above-mentioned liquid crystal composition of the present invention, such as polymerizable monomers, photopolymerization initiators, surfactants exerting an exclusion volume effect, and the like, can be contained. A filter can be produced by light irradiation using desired light amounts and patterns selected appropriately based on the above-mentioned method for changing the twist structure of liquid crystals.

The liquid crystal color filter of the present invention will be described in detail below by explanation of a method of producing a liquid crystal color filter.

The liquid crystal color filter of the present invention can be produced by using a material selected appropriately from the above-mentioned liquid crystal compositions of the present invention and known compositions containing a compound of the above-mentioned general formula (I) or (II).

In this case, the color filter may be in the form of a sheet constituted only of the above-mentioned liquid crystal composition, or comprising a desired substrate or temporary substrate carrying thereon a layer containing the liquid crystal composition (liquid crystal layer), and further, may comprise other layers (films) such as an orientation film, protective film and the like. In the latter case, two or more liquid crystal layers can be laminated. In this case, the exposure process described below is used a number of times.

As the above-mentioned nematic liquid crystal composition, polymerizable monomer, photopolymerization initiator and other components, the same compounds as can be used in the above-mentioned liquid crystal composition of the present invention can be used, and the contents, preferable ranges and the like are as in the case of the above-mentioned liquid crystal composition. It is preferable to simultaneously use a surfactant that exerts an exclusion volume effect.

Further, the content of a compound of the above-mentioned general formula (I) or (II) in the liquid crystal composition constituting the liquid crystal color filter is also the same as in the above-mentioned liquid crystal composition of the present invention.

The liquid crystal color filter of the present invention can be suitably produced, for example, from the above-mentioned liquid crystal composition of the present invention.

A method of producing the liquid crystal color filter is not particularly restricted and, for example, a production method can include at least one process in which exposure is conducted image-wise using a first light to effect patterning, then a second light to effect photopolymerization and cause hardening (hereinafter referred to as "exposure process" in some cases). Further, depending on a production embodiments selected, the filter may be formed via a process in which an orientation treatment is appropriately performed on a contact surface with the liquid crystal composition (orientation treatment process), a process in which the liquid crystal layer is transferred and formed by close-adhesion and releasing (transfer process), a process in which a cholesteric liquid crystal composition is applied to form a liquid crystal layer (application process), and other processes.

One specific embodiment using a cholesteric liquid crystal composition is shown below as an example of the above-mentioned production method including an exposure process.

[Exposure Process]

In this exposure process, each of patterning and fixation (hardening by polymerization) of a liquid crystal compound is conducted by light irradiation. Namely, patterning is conducted by exposure image-wise using a first light having a wavelength which can sensitize a light-reaction type optically active compound or light-reaction type chiral agent at high sensitivity. Then, the liquid crystal composition is hardened by photopolymerization using a second light which can sensitize a polymerization initiator at high sensitivity, to fix the helical structure of the liquid crystal composition for desired selective reflection colors.

When the liquid crystal composition is irradiated with the above-mentioned first light, the light-reaction type optically active compound or light-reaction type chiral agent therein is sensitized depending on illuminance of the light to change the helical structure of the liquid crystal compound. By this structural change, different selective reflection colors are manifested and image-wise patterns are formed. Therefore, light irradiation is conducted while changing irradiation strength for respective desired regions, and a plurality of colors are manifested corresponding to irradiation strengths. For example, by conducting exposure via a mask for exposure produced for changing light percent transmission image-wise, images can be formed by one-time light irradiation. That is, colored regions having different selective reflections can be formed simultaneously. This image can further be irradiated with the second light to be hardened (fixed), giving the liquid crystal color filter.

As the wavelength of the above-mentioned first light, wavelengths in the wavelength range in which the light-reaction type optically active compound or light-reaction type chiral agent is sensitized, particularly wavelengths adjacent to a light-sensitization peak wavelength of the optically active compound or the chiral agent, are preferable since sufficient patterning sensitivity is obtained. As the wavelength of the second light, wavelengths in a wavelength range in which the polymerization initiator is sensitized, particularly wavelengths adjacent to the light-sensitization peak wavelength of the polymerization initiator, are preferable since sufficient photopolymerization sensitivity is obtained.

The illuminances of the first and second lights (irradiation degree) are not particularly restricted, and can be appropriately selected depending on materials used, so as to sufficiently obtain light sensitivities in patterning and photopolymerization. As light sources used in irradiation of the first and second lights, the same light sources as those which can be used for irradiation of the above-mentioned liquid crystal composition can be used.

More specifically, production methods of the following first and second embodiments may be permissible, and a color filter can be produced more preferably by one of these two embodiments.

[First Embodiment]

(1) Process in which a liquid crystal composition in the form of an application solution is provided on a temporary substrate to form a transferring material having at least a liquid crystal layer The above-mentioned liquid crystal composition in the form of an application solution can be prepared by dissolving or dispersing components in a suitable solvent. Here, as this solvent, for example, 2-butanone, cyclohexanone, methylene chloride, chloroform and the like are listed. In production of a liquid crystal color filter, a cholesteric liquid crystal composition is preferable.

Between the above-mentioned liquid crystal layer and temporary substrate, a cushioning layer containing a thermoplastic resin and the like can also be provided, when extraneous substances and the like are present on a receiving body or the like, from the stand point of securing close-adhesion in transferring. It is preferable to perform orientation treatments (orientation treatment process) such as rubbing and the like on the surface of the cushioning layer and the like.

(2) Process in which the above-mentioned transferring material is laminated on a substrate permitting light transmission An image-receiving material having an image-receiving layer on a substrate may also be used, in addition to the above-mentioned substrate permitting light transmission. Further, a liquid crystal composition may be directly applied and formed on a substrate without using the above-mentioned transferring material (application process). The application method can be appropriately selected from known application methods using a bar coater, spin coating and the like. Of these, a transferring method is preferable from the standpoints of material loss and cost.

(3) Process in which transferring material is peeled from substrate permitting light transmission, and cholesteric liquid crystal layer is formed on the above-mentioned substrate (transferring process)

The above-mentioned liquid crystal layer can also be constituted of plural layers further laminated after the following process (4)

(4) Process in which cholesteric liquid crystal layer is irradiated with ultraviolet radiation having illuminance of $v^1$ via mask for exposure to form picture element pattern showing selective reflection color, and this is irradiated with ultraviolet radiation having illuminance of $v^2$ to harden layer (exposure process)

[Second Embodiment]

(1) Process in which liquid crystal composition is directly provided on substrate constituting color filter, to form liquid crystal layer In this process, a liquid crystal composition prepared in the form of an application solution in the same manner as described above can be applied by a known application method using a bar coater, spin coater or the like, to form a liquid crystal layer.

Further, between the above-mentioned cholesteric layer and substrate, the same orientation film as described above may also be formed. It is preferable to perform orientation treatments (orientation treatment process) such as rubbing and the like on the surface of the orientation film.

(2) Same exposure process as process (4) in the above-mentioned first embodiment The thickness of the liquid crystal layer functioning as the liquid color filter (liquid crystal composition in the form of a sheet) is preferably from 1.5 to 5 $\mu$m.

Further explanations are provided below using FIG. 1. FIG. 1 is sectional views showing one embodiment of a process of producing the liquid crystal color filter of the present invention.

First, the above-mentioned components are dissolved in a suitable solvent, to prepare a cholesteric liquid crystal composition in the form of an application solution. Herein, the components and solvent are as described above.

Figure 1B:
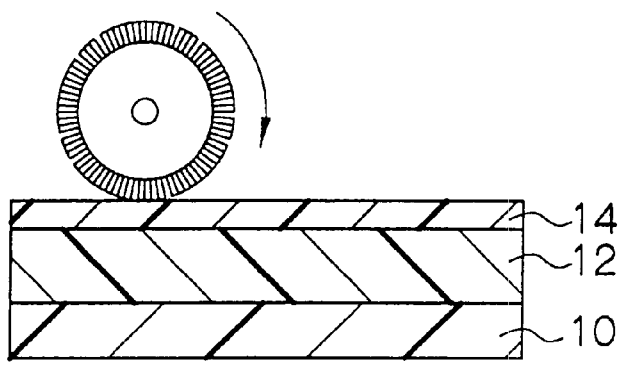
FIG. 1B is a sectional view showing a process of producing a liquid color filter of the present invention.

As illustrated in FIG. 1A, a substrate 10 (hereinafter, also referred to as "temporary substrate") is prepared, and on this substrate 10, for example, an acrylic resin, polyester, polyurethane or the like is applied to form a cushioning layer (thermoplastic resin layer) 12, and further an orientation film 14 composed of polyvinyl alcohol and the like is laminated. On this orientation film, rubbing treatment is performed as shown in FIG. 1B. Though this rubbing treatment is not necessarily required, an orientation property can be more improved when the rubbing treatment is conducted.

Figure 1C:
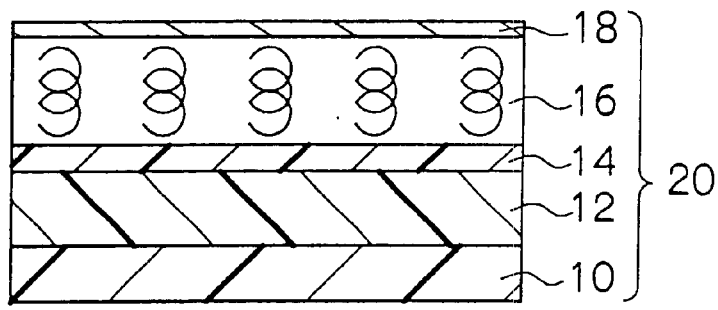
FIG. 1C is a sectional view showing a process of producing a liquid color filter of the present invention.

Then, as shown in FIG. 1C, on the above-mentioned orientation film 14, a cholesteric liquid crystal composition in the form of an application solution is applied and dried to form a cholesteric liquid crystal layer 16. Then, a cover film 18 is provide on this cholesteric liquid crystal layer 16 to provide a transferring material. Hereinafter, this transferring material is referred to as a transferring sheet 20.

Figure 1D:
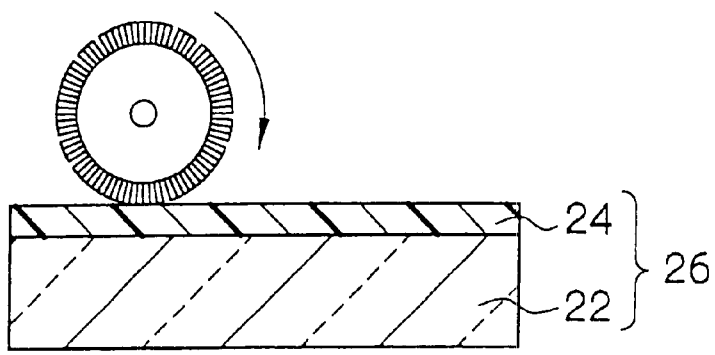
FIG. 1D is a sectional view showing a process of producing a liquid color filter of the present invention.

On the other hand, as shown in FIG. 1D, another substrate 22 is prepared, an orientation film 24 is formed on this substrate as described above, and rubbing treatment is performed on the surface thereof. Hereinafter, this is referred to as a substrate 26 for a color filter.

Figure 1E:
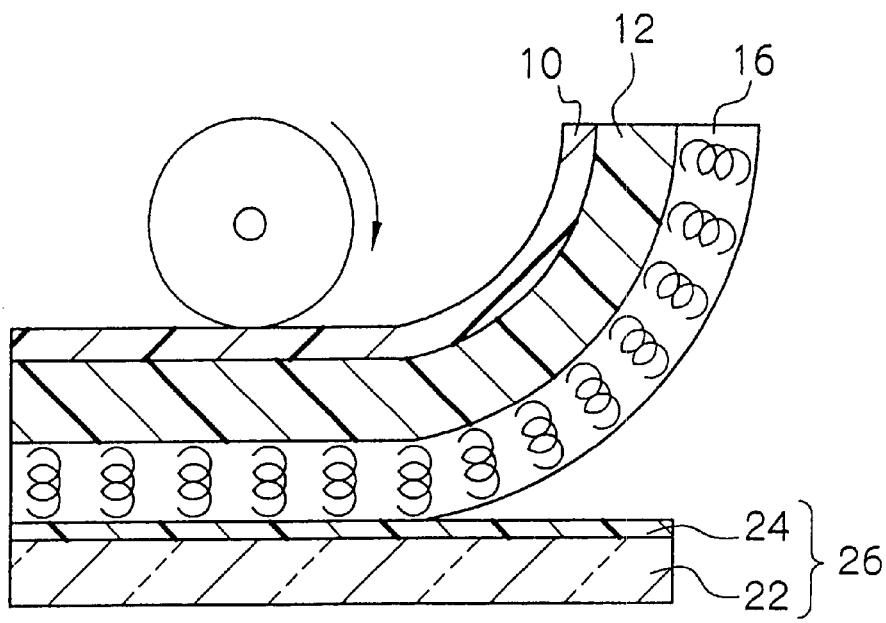
FIG. 1E is a sectional view showing a process of producing a liquid color filter of the present invention.
Figure 1F:
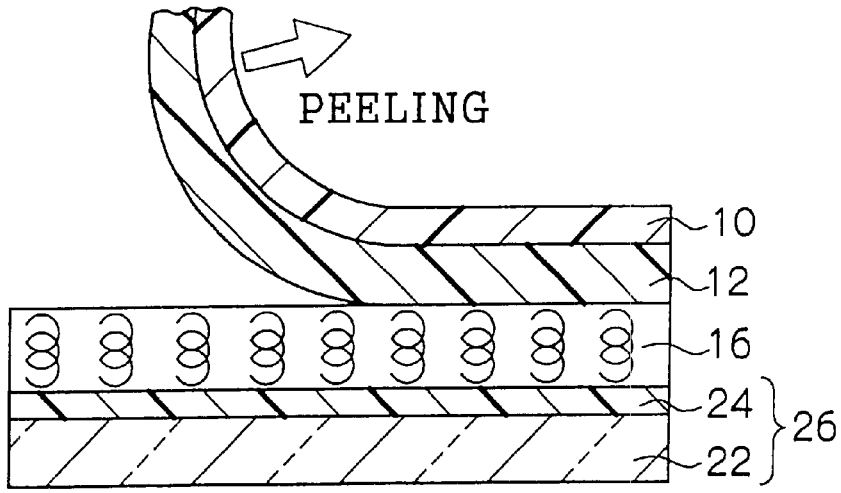
FIG. 1F is a sectional view showing a process of producing a liquid color filter of the present invention.

Next, the cover film 18 of the transferring sheet 20 is peeled, then, as shown in FIG. 1E, the surface of the cholesteric liquid crystal layer 16 of the transferring sheet 20 and the surface of the orientation film 24 of the substrate 26 for the color filter are joined so that they are in contact with each other, and laminated by passing through a roll, rotating along a direction represented by an arrow in the figure. Then, as shown in FIG. 1F, peeling is caused between the orientation film 14 and the cushioning layer 12 of the transferring sheet 20, and the cholesteric liquid crystal layer is transferred together with the orientation film 14 onto the substrate 26 for the color filter. In this case, the cushioning layer 12 need not necessarily be peeled together with the temporary substrate 10.

Figure 1G:
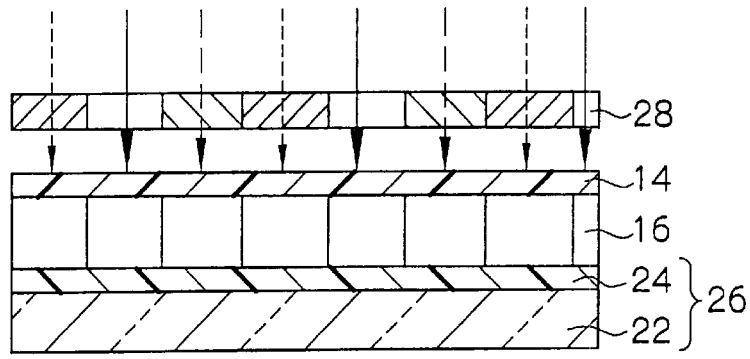
FIG. 1G is a sectional view showing a process of producing a liquid color filter of the present invention.

After transferring, as shown in FIG. 1G, an exposure mask 28 having a plurality of regions having different light percent transmissions is placed above the orientation film 14, and the cholesteric liquid crystal layer 16 is irradiated pattern-wise with a first light via this mask 28. The cholesteric liquid crystal layer 16 contains liquid crystal compounds, chiral compounds and the like such that helical pitch varies depending on the light irradiation amount, and structures having different helical pitches are formed such that, for example, a region which reflects green color (G) and allows transmission of blue color (B) and red color (R), a region which reflects blue color (B) and allows transmission of green color (G) and red color (R), and a region which reflects red color (R) and allows transmission of green color (G) and blue color (B) are formed for each pattern.

Figure 1H:
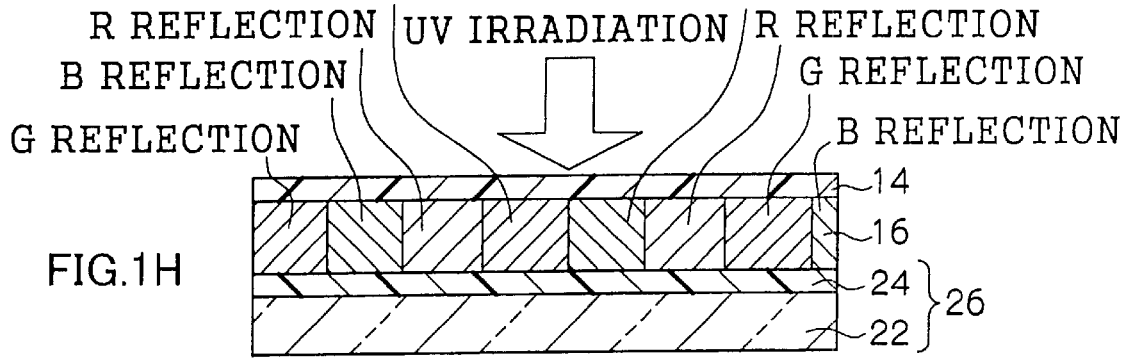
FIG. 1H is a sectional view showing a process of producing a liquid color filter of the present invention.
Figure 1I:
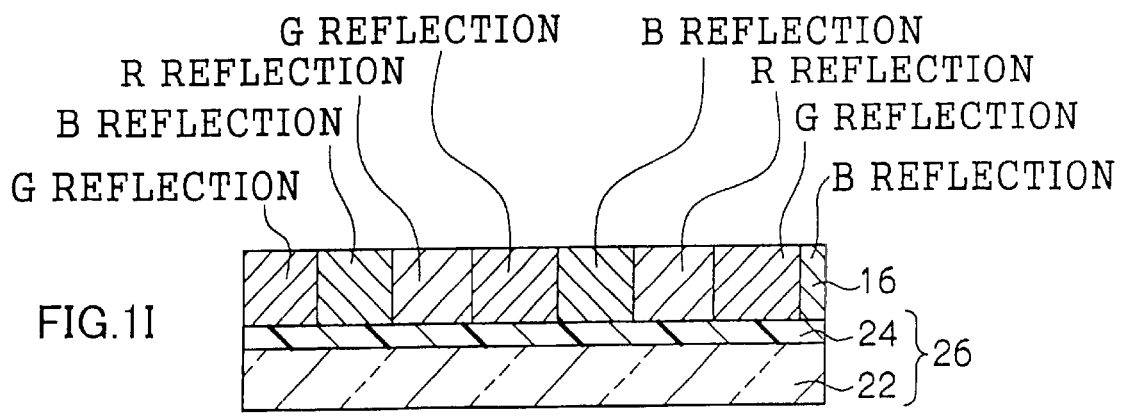
FIG. 1I is a sectional view showing a process of producing a liquid color filter of the present invention.

Next, as shown in FIG. 1H, the cholesteric liquid crystal layer 16 is further irradiated with ultraviolet radiation at a different irradiation strength than in the light irradiation in the above-mentioned process of FIG. 1G, to fix patterns. Then, unnecessary portions on the cholesteric liquid crystal layer 16 (for example, remaining portions of the cushioning layer, intermediate layer and the like, and unexposed portions) can be removed by using 2-butanone, chloroform or the like, to form a cholesteric liquid crystal layer having reflection regions of R, G and B as shown in FIG. 1I.

The method shown in FIG. 1 is one embodiment of a method of producing a color filter according to a lamination mode, and it may also be a production method according to an application mode in which a liquid crystal layer is directly applied and formed on a substrate for a color filter. In this case, a cholesteric liquid crystal layer is applied on the orientation film 24 of the substrate 26 for the color filter shown in FIG. 1D, dried, and then the processes shown in FIGS. 1G to 1I as described above are carried out sequentially.

These processes, transferring materials used, materials of a substrate and the like, are described in detail in specifications of Japanese Patent Application Nos. 11-342896 and 11-343665 submitted previously by the present inventors.

As described above, when a liquid crystal composition containing a light-reaction type optically active compound of the general formula (I) or a light-reaction type chiral agent of the present invention is used, the change rate of the twisting power of the helical structure of liquid crystals based on light amounts is large. Consequently, color width of selective reflection colors which can be manifested by the liquid crystals is enlarged, and a liquid crystal color filter composed of three primary colors, blue (B), green (G) and red (R), excellent in color purities can be obtained.

<Optical Film>

The optical film of the present invention contains at least one selected from the above-mentioned light-reaction type optically active compounds or light-reaction type chiral agents of the present invention. Embodiments further containing at least one liquid crystalline compound (preferably, a nematic liquid crystal compound) are preferable. Optical wavelengths can be selected as desired in a wide wavelength range. Further, the optical film of the present invention contains, if necessary, other components as listed for the above-mentioned liquid crystal composition of the present invention such as polymerizable monomers, photopolymerization initiators, and surfactants exerting an exclusion volume effect and the like. This film can be produced by conducting light irradiation with desired patterns and light amounts selected appropriately, based on the above-mentioned "method for changing twist structure of liquid crystal".

The optical film of the present invention can be produced by using a material selected appropriately from the above-mentioned liquid crystal compositions of the present invention and known compositions containing a compound of the above-mentioned general formula (I) or (II). Here, the form of the optical film is not particularly restricted, and may be any of a sheet constituted only of the above-mentioned liquid crystal composition, a desired substrate or temporary substrate carrying thereon a layer containing the liquid crystal composition (liquid crystal layer), and other forms, and further, may comprise other layers (films) such as an orientation film, protective film and the like.

As the above-mentioned liquid crystalline compound, polymerizable monomer, photopolymerization initiator and other components, the same compounds as can be used in the above-mentioned liquid crystal composition of the present invention can be used, and the contents, preferable ranges and the like are as in the case of the above-mentioned liquid crystal composition. Further, the content of a compound of the above-mentioned general formula (I) or (II) in the liquid crystal composition constituting the optical film is also be same as in the above-mentioned liquid crystal composition of the present invention.

The optical film of the present invention can be preferably produced using, for example, the above-mentioned liquid crystal composition of the present invention.

This method of producing an optical film can be approximately the same method as for the above-mentioned liquid crystal color filter, and may also be a method containing the above-mentioned exposure process at least one time. Further, depending on production embodiments selected, an optical filter may be formed via a process such as the above-mentioned orientation treatment process, transferring process, application process and the like.

More specifically, an optical filter can also be produced by approximately the same method as the production methods of the above-mentioned first embodiment and second embodiment.

As described above, when a liquid crystal composition containing a light-reaction type optically active compound or a light-reaction type chiral agent of the general formula (I) or (II) is used, the twisting power of the helical structure of liquid crystals with light amount can be varied significantly. Consequently, an optical film of a non-light absorption type can be obtained. For example, the liquid crystal phase is a cholesteric liquid crystal phase, the color width of selective reflection of the liquid crystals is large, and an optical film having a variety of selective reflection colors, an optical film composed of primary colors (B, G, R) excellent in color purities, or the like can be obtained.

<Recording Medium>

The recording medium of the present invention contains at least one selected from the above-mentioned light-reaction type optically active compound or light-reaction type chiral agents of the present invention, and embodiments further containing at least one liquid crystalline compound (preferably, nematic liquid crystal compound) are preferable. Further, the recording medium of the present invention contains, if necessary, other components as listed for the above-mentioned liquid crystal composition of the present invention such as polymerizable monomers, photopolymerization initiators, and surfactants exerting an exclusion volume effect and the like, and the like.

The form of the recording medium of the present invention is not particularly restricted, and may be a sheet constituted only of a liquid crystal composition, or a desired support or temporary support (hereinafter, referred to as "support and the like") carrying thereon a layer comprising a liquid crystal composition containing a light-reaction type optically active compound or a light-reaction type chiral agent (liquid crystal layer). Here, the liquid crystal composition can be appropriately selected from the above-mentioned liquid crystal compositions of the present invention and known compositions containing a compound of the above-mentioned general formula (I) or (II). Further, other layers (films) such as an orientation film, protective film and the like may also be provided.

As the above-mentioned liquid crystalline compound, polymerizable monomer, photopolymerization initiator and other components, the same compounds as can be used in the above-mentioned liquid crystal composition can be used, and the contents, preferable ranges and the like are as in the case of the liquid crystal composition. Further, the content of a compound of the above-mentioned general formula (I) or (II) in a liquid crystal composition constituting a recording medium is also be same as in the above-mentioned liquid crystal composition of the present invention.

The recording medium of the present invention can be preferably produced by providing the above-mentioned liquid crystal composition of the present invention on a support and the like, for example.

As the method of producing the liquid crystal composition on the support and the like, there are (1) a method in which a transferring material comprising a temporary support carrying thereon a liquid crystal layer containing the liquid crystal composition of the present invention is used, and the liquid crystal layer is transferred onto a support, (2) a method in which a liquid crystal composition prepared in the form of an application solution is directly applied on the support and the like, and other methods.

In the above-mentioned methods (1) and (2), transferring materials and application methods and the like can be adapted according to the embodiments exemplified for the above-mentioned liquid crystal composition of the present invention (first and second embodiments) and the explanations of FIG. 1.

The recording medium of the present invention produced as described above can be irradiated with light at desired patters and light amounts appropriately selected to form an image based on the change rate of the twisting power of a liquid crystal, and, particularly in the case of a cholesteric liquid crystal, can be irradiated to form a color image formed by selective reflection colors determined by the change rate of the helical pitch. The formation of the image may be conducted based on the above-mentioned "method for changing twist structure of liquid crystal" and "method for fixing twist structure of liquid crystal".

In addition, when a light-reaction type optically active compound or a light-reaction type chiral agent of the general formula (I) or (II) is used as a chiral agent which changes the structure of a liquid crystal, the change rate of the twisting power of the helical structure of the liquid crystal depending on light amount is large. Consequently, images having a wide color reproduction range can be formed and, particularly in the case of a cholesteric liquid crystal, a width of hues selectively reflected by a liquid crystal can be enlarged, and multi-color images having high color purities can be formed. Further, high change rate of the twisting power also contributes significantly to an increase in sensitivity (increase in speed) in forming images.

Further, by using, for example, a polymerizable liquid crystal compound or a polymerizable monomer a liquid crystal after patterning can be fixed, and images having sufficiently excellent image stability can be formed.

As the light sources used in irradiation or fixing, the same light sources as those which can be used for the above-mentioned liquid crystal composition of the present invention can be used, giving preferable photorecording.

As described above, when a light-reaction type optically active compound or a light-reaction type chiral agent of the general formula (I) or (II) is used as a chiral agent which changes the helical structure of a liquid crystal molecule, the twisting power (twist angle) of liquid crystals can be significantly changed. Particularly in the case of a cholesteric liquid crystal using a nematic liquid crystal compound, the selective reflection wavelength range obtained by light irradiation is enlarged, and consequently color purities of three primary colors can also be enhanced. As a result, selectivity and clearness of the hues of the liquid crystals increase, and, particularly in a liquid crystal color filter, optical film or the like, clear and brilliant color images can be displayed, and in a recording medium, images of multiple hues can be formed.

EXAMPLES

The following examples further illustrate the present invention, but do not limit the scope of the present invention. In the examples, "parts" and "%" are all "parts by weight" and "% by weight".

Example 1

Measurement of Change of Helical Pitch by Light Irradiation 2 parts of a light-reaction type chiral agent of the present invention (exemplified compound (6)) synthesized by a method analogous to the above-mentioned synthesis method and 98 parts of a nematic liquid crystal composition (ZLI-1132, manufactured by Merck) were mixed, and poured into a wedge type cell (glass thickness 1.1 mm, blue plate) on which uni-axial orientation treatment had been performed by a polyimide orientation film. Here, helical pitch at room temperature was measured using a polarization microscope and was found to be 1.47 $\mu$m. This was calculated in terms of helical twisting power (HTP) to give a value of 34 $\mu m^{-1}$.

Next, the above-mentioned wedge type cell was irradiated with ultraviolet radiation for 3 minutes at an irradiation strength of 300 mW/cm$^2$ from a high pressure mercury lamp. After irradiation, helical pitch at room temperature was measured in the same manner as described above, to find a pitch changed to 2.8 $\mu$m. This was calculated in terms of HTP to give a value of 18 $\mu m^{-1}$. Therefore, the change rate of HTP was 1.89.

As described above, the twisting power of helices (HTP) could be significantly changed by irradiation with ultraviolet radiation. Further, the twist direction before and after irradiation with ultraviolet radiation was confirmed by a contact method and was found to be right-twisting both before and after irradiation.

Example 2

Production of Wide Band Circular Polarization Reflection Plate (1) Preparation of Substrate On a glass substrate, a polyimide orientation film (LX-1400, manufactured by Hitachi Chemical Dupont) application solution was applied by a spin coater, dried for 5 minutes in an oven at 100° C., and then baked for 1 hour in an oven at 250° C. to form an orientation film. Further, the surface of the film was subjected to orientation treatment by rubbing treatment to produce a glass substrate equipped with an orientation film.

(2) Production

On the orientation film of the glass substrate equipped with the orientation film obtained above, an application solution prepared by the following recipe was applied by a bar coater, and kept for 5 minutes on a hot plate at 110° C., and then irradiated with light by an ultrahigh pressure mercury lamp via a band pass filter having a light source center wavelength at 365 nm for 3 minutes, at the same temperature. The following light-reaction type chiral agent of the present invention (exemplified compound (5)) was synthesized by a method analogous to the above-mentioned synthesis method.

Next, the plate was kept in a dark place for 5 minutes while being maintained at 110° C. Then the band pass filter was removed, and the whole surface was irradiated with light by the same ultrahigh pressure mercury lamp as described above at an irradiation energy of 500 mJ/cm$^2$, while spraying a nitrogen gas, to give hardening by polymerization. As described above, a circular polarization reflection plate was produced.

[Recipe of application solution]

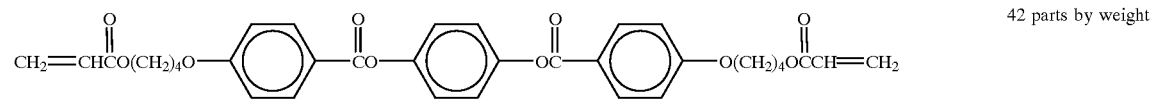

42 parts by weight

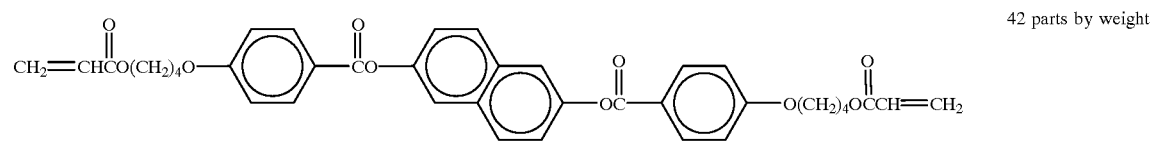

42 parts by weight

Exemplified compound (5): light-reaction type optically active compound (chiral agent)

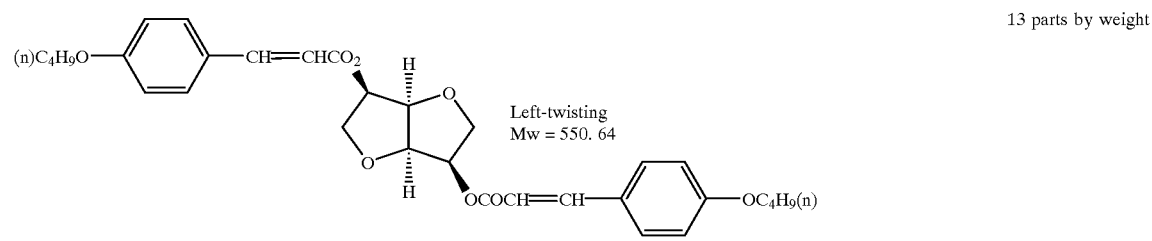

Left-twisting
Mw = 550. 64

13 parts by weight

2 parts by weight

5 parts by weight

Chloroform 400 parts by weight

The circular polarization reflection plate obtained above manifested selective reflections in a wide wavelength range ranging from 450 nm to 680 nm, that is, had a band property sufficient for a wide-band circular polarization reflection plate. Further, right circular polarization reflectance at a selective reflection wavelength of 550 nm was 95%.

Example 3
Production of Liquid Crystal Color Filter
(1) Preparation of Filter Substrate On a glass substrate, a polyimide orientation film (LX-1400, manufactured by Hitachi Chemical Dupont) application solution was applied by a spin coater, dried for 5 minutes in an oven at 100° C., and then baked for 1 hour in an oven at 250° C. to form an orientation film. Further, the surface of the film was subjected to orientation treatment by rubbing treatment to produce a glass substrate equipped with an orientation film.

(2) Production of Filter Layer

On the orientation film of the glass substrate equipped with the orientation film obtained above, an application solution for a photosensitive resin layer prepared by the following recipe was applied by a spin coater, and dried for 2 minutes in an oven at 100° C. to form a photosensitive resin layer. The following light-reaction type chiral agent of the present invention (exemplified compound (2)) was synthesized by the above-mentioned synthesis method.

[Recipe of application solution for photosensitive resin layer]

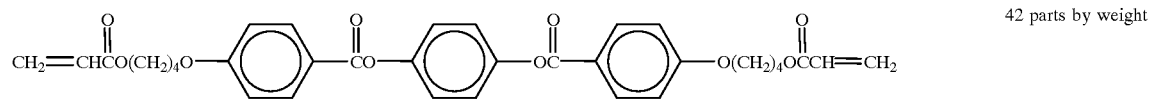

42 parts by weight

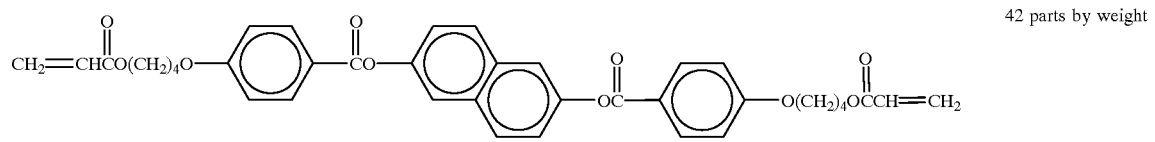

42 parts by weight

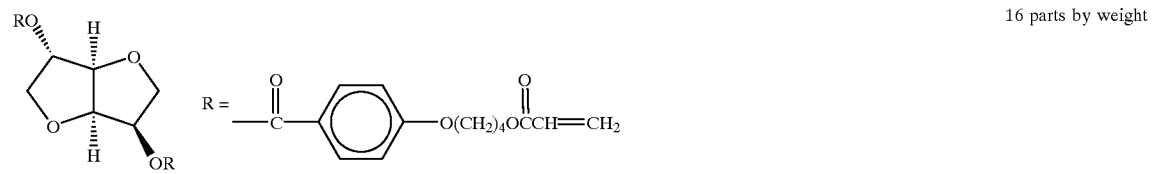

16 parts by weight

Exemplified compound (2): light-reaction type optically active compound (chiral agent)

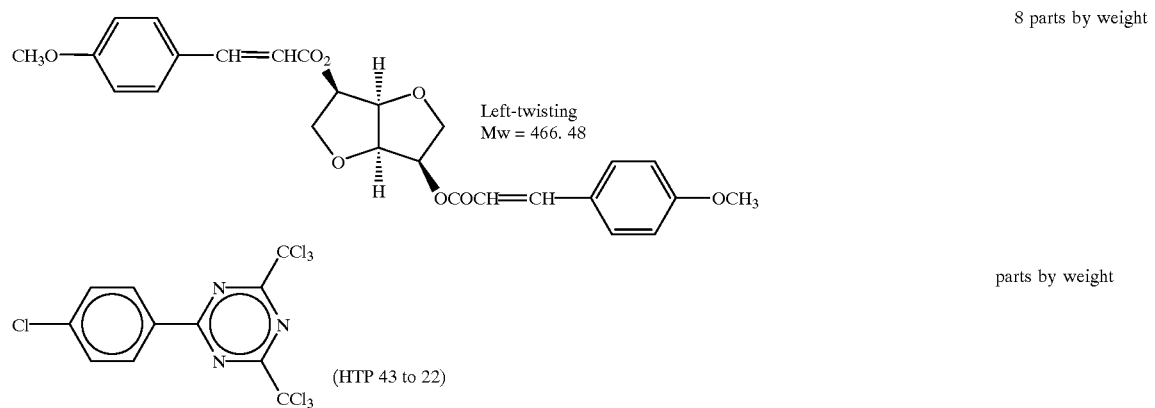

8 parts by weight

Left-twisting
Mw = 466.48

(HTP 43 to 22)

parts by weight

Dipentaerythritol hexaacrylate    3 parts by weight

Chloroform    400 parts by weight

Next, the plate was kept for 5 minutes on a hot plate of 100° C. so as to give contact at the surface of the glass substrate, to cause color development of the photosensitive resin layer. Further, on this photosensitive resin layer, an ultrahigh pressure mercury lamp was placed via a photomask carrying regions having different transmittances at three grades (0%, 46%, 92%) and being arranged corresponding to blue picture elements, green picture elements and red color elements, and a band pass filter having a central wavelength of 365 nm. The resin layer was irradiated with light by the ultrahigh pressure mercury lamp though the photomask and band pass filter, to realize patterning. At this stage, the irradiation energy was 300 mJ/cm² formed picture elements and the irradiation strength was 30 mW/cm².

Next, the photomask and band pass filter were removed, and the layer was irradiated on the whole surface with light by the same ultrahigh pressure mercury lamp as described above at an irradiation energy of 500 mJ/cm², while spraying a nitrogen gas, to give hardening by polymerization. Further, for promoting the degree of hardening of the filter part (photosensitive resin layer), the layer was baked for 20 minutes in an oven at 220° C., to obtain a color filter having patterns of red picture elements, green picture elements and blue picture elements formed therein.

In the above-mentioned patterning, the helical pitch of liquid crystals (twisting power of liquid crystals) could be significantly changed by irradiation and picture element patterns of a red color, green color and blue color having high color purities could be formed.

Example 4

Production of Optical Compensation Film for STN Element

On triacetylcellulose (TAC) having a thickness of 80 μm, a polyethylene vinyl alcohol (PVA) film having a saponification degree of 99.5% was formed by a bar coat method, and heated at 110° C. for 3 minutes. Rubbing treatment was performed on this PVA film. Further, an application solution prepared by the following recipe was applied on the PVA film with a bar coater while heating, and this was dried in an oven at 120° C. for 3 minutes to form a film. The following light-reaction type chiral agent of the present invention (exemplified compound (7)) was synthesized by the above-mentioned synthesis method.

[Recipe of application solution]

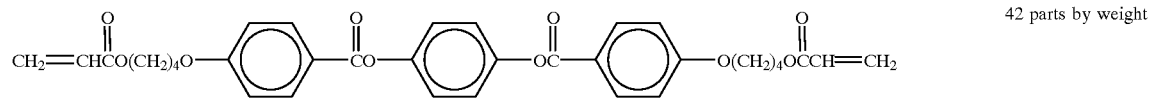

42 parts by weight

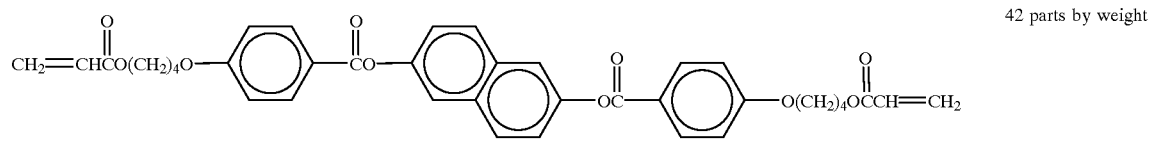

42 parts by weight

Exemplified compound (7): light-reaction type optically active compound (chiral agent)

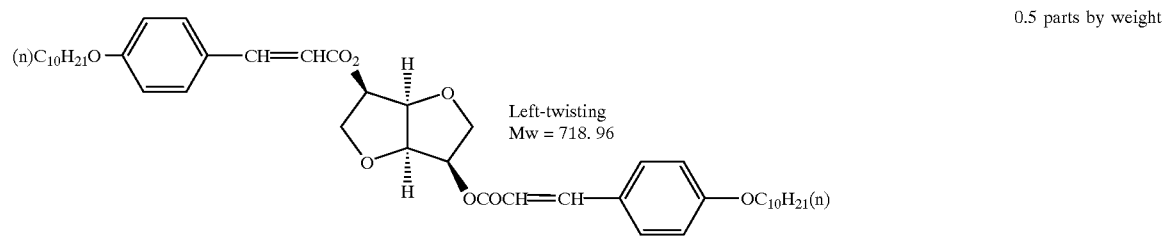

0.5 parts by weight

Left-twisting
Mw = 718. 96

3 parts by weight

Chloroform 400 parts by weight

Next, the film was polymerized to be hardened by irradiation over the film with ultraviolet radiation using an high pressure mercury lamp (irradiation energy 300 mJ/cm$^2$) at 100° C., to produce an optical compensation film for an STN element (hereinafter, referred to as "STN compensation film"). The film thickness of the STN compensation film at this stage was measured and was found to be 5.0 μm. From the polarization transmission spectrum profile of the STN compensation film, it was found that the orientation (helical structure) of liquid crystal molecules was twisted to the film thickness direction by 240° and the twist angle of the helix (rotation angle) was 240°.

Further, an STN compensation film having a twist angle in a reverse direction to that of the above-mentioned film was prepared, and these were laminated such that liquid crystal molecules would cross at right angles at the joined parts, inserted between two polarization plates having absorption axes crossing each other at right angles, and observed visually to confirm excellent black color. Therefore, it was confirmed that the film (STN compensation film) formed as described above acted as an optical compensation film for an STN element.

Example 5
Prevention of Occurrence of Reverse Twist Domain for TN Element

On an ITO film of a glass substrate equipped with an ITO film, a polyimide orientation film (LX-1400, manufactured by Hitachi Chemical Dupont) application solution was applied by a spin coater, dried for 5 minutes in an oven at 100° C., and then baked for 1 hour in an oven at 250° C. to form an orientation film. Further, the surface of the film was subjected to orientation treatment by performing rubbing treatment such that a rubbing angle was 90°, to produce two glass substrates equipped with orientation films.

The glass substrates were placed so that the orientation films faced each other, and pasted by a two-part epoxy resin adhesive into which spacer beads having a diameter of 6 μm had been mixed, to form a cell for driving. The thickness of this cell was measured by a light interference method and was found to be 5.4 μm.

Into the above-mentioned cell, the following composition was poured. The following light-reaction type chiral agent of the present invention (exemplified compound (2)) was synthesized by the above-mentioned synthesis method.
[Composition]
  Nematic liquid crystal composition (ZLI-1132, manufactured by Merck) 99.9%
  Light-reaction type chiral agent of the present invention (exemplified compound (2) described previously) 0.1%

After the pouring, the cell for driving was inserted between two polarization plates whose absorption axes crossed at right angle, and observed visually, to find no occurrence of reverse twist domain. Therefore, there was no reduction in contrast by occurrence of reverse twist, and images excellent in contrast and color purities would be expected to be displayed.

Example 6

Measurement of Change of Helical Pitch by Light Irradiation 2 parts of a light-reaction type chiral agent of the present invention (exemplified compound (14)) synthesized by the above-mentioned synthesis method (Synthesis of light-reaction type chiral agent (14)) and 98 parts of a nematic liquid crystal composition (ZLI-1132, manufactured by Merck) were mixed, and poured into a wedge type cell (glass thickness 1.1 mm, blue plate) on which uni-axial orientation treatment had been performed by a polyimide orientation film. Here, helical pitch at room temperature was measured using a polarization microscope and was found to be 1.14 $\mu$m. This was calculated in terms of helical twisting power (HTP) to give a value of 44 $\mu m^{-1}$.

Next, the above-mentioned wedge type cell was irradiated with ultraviolet radiation for 3 minutes at an irradiation strength of 300 mW/cm$^2$ from a high pressure mercury lamp. After irradiation, helical pitch at room temperature was measured in the same manner as described above to find a pitch changed to 3.6 $\mu$m. This was calculated in terms of HTP to give a value of 14 $\mu$m. Therefore, the change rate of HTP was 3.14.

As described above, the twisting power of helix (HTP) could be significantly changed by irradiation with ultraviolet radiation. Further, the twist direction before and after irradiation with ultraviolet radiation was confirmed by a contact method and was found to be right-twisting both before and after irradiation.

Example 7

Production of Wide Band Circular Polarization Reflection Plate (1) Preparation of Substrate On a glass substrate, a polyimide orientation film (LX-1400, manufactured by Hitachi Chemical Dupont) application solution was applied by a spin coater, dried for 5 minutes in an oven at 100° C., and then baked for 1 hour in an oven at 250° C. to form an orientation film. Further, the surface of the film was subjected to orientation treatment by rubbing treatment to produce a glass substrate equipped with an orientation film.

(2) Production

On the orientation film of the glass substrate equipped with the orientation film obtained above, an application solution prepared by the following recipe was applied by a bar coater, and kept for 5 minutes on a hot plate of 110° C., and then irradiated with light by an ultrahigh pressure mercury lamp via a band pass filter having a light source central wavelength at 365 nm for 5 minutes, at the same temperature. The following light-reaction type chiral agent of the present invention (exemplified compound (15)) was synthesized by a method analogous to the above-mentioned synthesis method.

Next, the plate was kept in a dark place for 5 minutes while being maintained at 110° C. Then, the band pass filter was removed, and the whole surface was irradiated with light by the same ultrahigh pressure mercury lamp as described above at an irradiation energy of 500 mJ/cm$^2$, while spraying a nitrogen gas, to give hardening by polymerization. As described above, a circular polarization reflection plate was produced.

[Recipe of application solution]

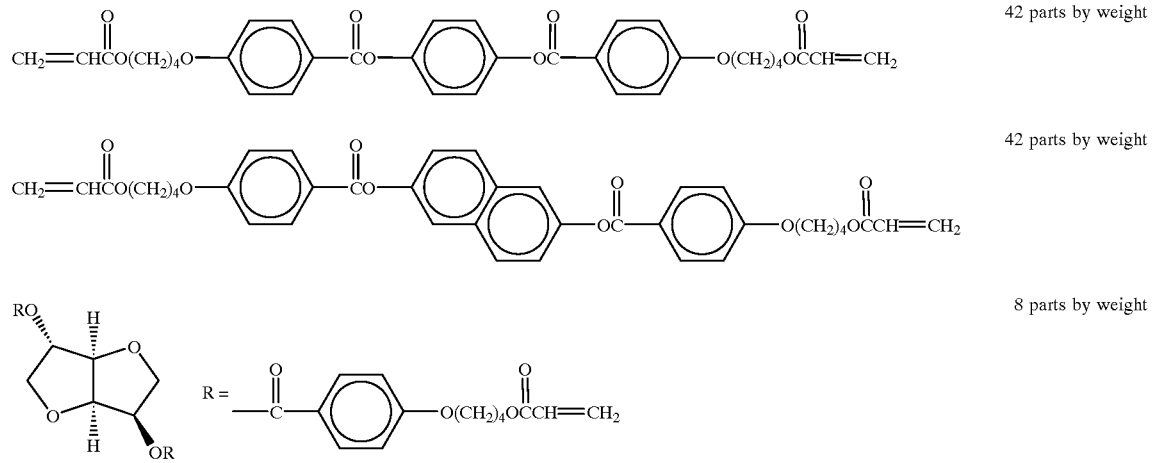

Exemplified compound (15): light-reaction type chiral agent

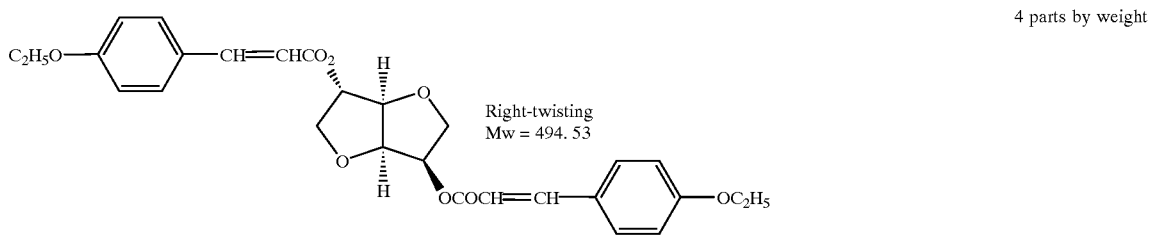

| [Recipe of application solution] | |
|---|---|
| [structure: 4-chlorophenyl-bis(trichloromethyl)triazine] | 2 parts by weight |
| [structure: 2-(2H-benzotriazol-2-yl)-resorcinol] | 5 parts by weight |
| Chloroform | 400 parts by weight |

The circular polarization reflection plate obtained above manifested selective reflections in a wide wavelength range ranging from 450 nm to 630 nm, that is, had a band property sufficient for a wide-band circular polarization reflection plate. Further, right circular polarization reflectance at a selective reflection wavelength of 550 nm was 98%.

Example 8
Production of Liquid Crystal Color Filter
(1) Preparation of Filter Substrate On a glass substrate, a polyimide orientation film (LX-1400, manufactured by Hitachi Chemical Dupont) application solution was applied by a spin coater, dried for 5 minutes in an oven at 100° C., and then baked for 1 hour in an oven at 250° C. to form an orientation film. Further, the surface of the film was subjected to orientation treatment by rubbing treatment to produce a glass substrate equipped with an orientation film.

(2) Production of Filter Layer

On the orientation film of the glass substrate equipped with the orientation film obtained above, an application solution for a photosensitive resin layer prepared by the following recipe was applied by a spin coater, and dried for 2 minutes in an oven at 110° C., to form a photosensitive resin layer. The following light-reaction type chiral agent of the present invention (exemplified compound (14)) was synthesized by the above-mentioned synthesis method.

| [Recipe of application solution for photosensitive resin layer] | |
|---|---|
| $CH_2=CHCO(CH_2)_4O-$[structure: triphenyl diester chain]$-O(CH_2)_4OCCH=CH_2$ | 42 parts by weight |
| $CH_2=CHCO(CH_2)_4O-$[structure: phenyl-naphthyl-phenyl diester chain]$-O(CH_2)_4OCCH=CH_2$ | 42 parts by weight |
| [structure: isosorbide diester with R = $-C(O)-C_6H_4-O(CH_2)_4OCCH=CH_2$] | 8 parts by weight |

-continued

[Recipe of application solution for photosensitive resin layer]

Exemplified compound (14): light-reaction type chiral agent

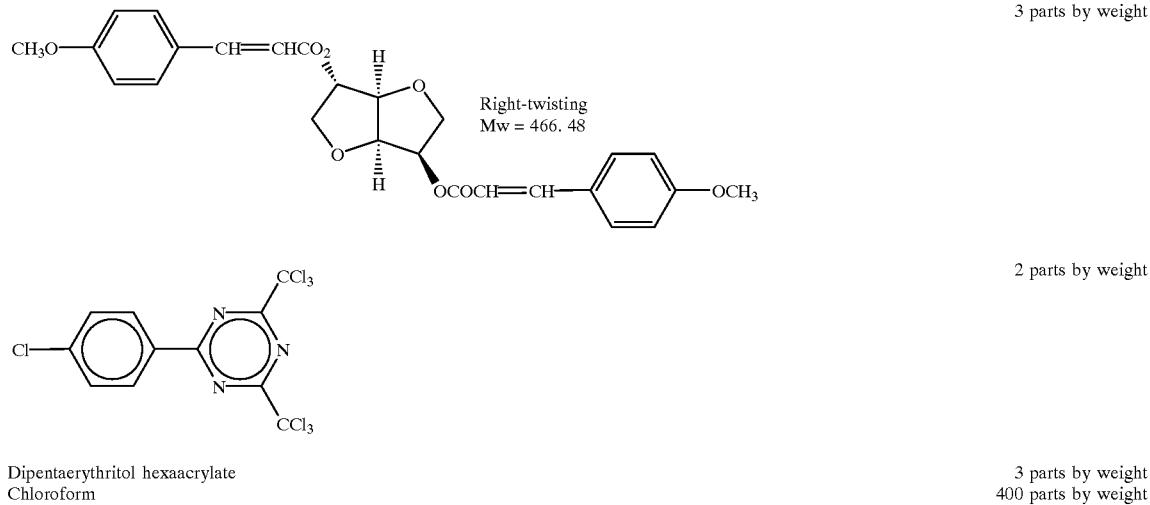

Right-twisting
Mw = 466.48

3 parts by weight 2 parts by weight

Dipentaerythritol hexaacrylate  3 parts by weight
Chloroform  400 parts by weight Next, the plate was kept for 5 minutes on a hot plate of 110° C. so as to give contact at the surface of the glass substrate, to cause color development of the photosensitive resin layer. Further, on this photosensitive resin layer, an ultrahigh pressure mercury lamp was placed via a photomask carrying regions having different transmittances at three grades (0%, 46%, 92%) and being arranged corresponding to blue picture elements, green picture elements and red color elements, and a band pass filter having a central wavelength of 365 nm. The resin layer was irradiated with light by the ultrahigh pressure mercury lamp though the photomask and band pass filter, to realize patterning. At this stage, the irradiation energy was 300 mJ/cm$^2$ for red picture elements and the irradiation strength was 30 mW/cm$^2$.

Next, the photomask and band pass filter were removed, and the layer was irradiated on the whole surface with light by the same ultrahigh pressure mercury lamp as described above at an irradiation energy of 500 mJ/cm$^2$, while spraying a nitrogen gas, to give hardening by polymerization. Further, for promoting the degree of hardening of the filter part (photosensitive resin layer), the layer was baked for 20 minutes in an oven at 220° C., to obtain a color filter having patterns of red picture elements, green picture elements and blue picture elements formed therein.

In the above-mentioned patterning, the helical pitch of a liquid crystal (twisting power of liquid crystal) could be significantly changed by irradiation and picture element patterns of a red color, green color and blue color having high color purities could be formed.

Example 9
Production of Optical Compensation Film for STN Element

On triacetylcellulose (TAC) having a thickness of 80 μm, a polyethylene vinyl alcohol (PVA) film having a saponification degree of 99.5% was formed by a bar coat method, and heated at 110° C. for 3 minutes. Rubbing treatment was performed on this PVA film. Further, an application solution prepared by the following recipe was applied on the PVA film by a bar coater while heating, and this was dried in an oven at 120° C. for 3 minutes, to form a film. The following light-reaction type chiral agent of the present invention (exemplified compound (17)) was synthesized by the above-mentioned synthesis method.

[Recipe of application solution]

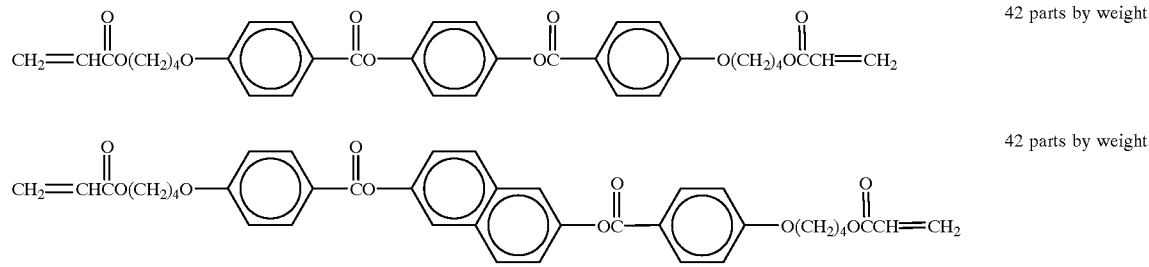

42 parts by weight 42 parts by weight

-continued

[Recipe of application solution]

Exemplified compound (17): light-reaction type chiral agent | 0.3 parts by weight

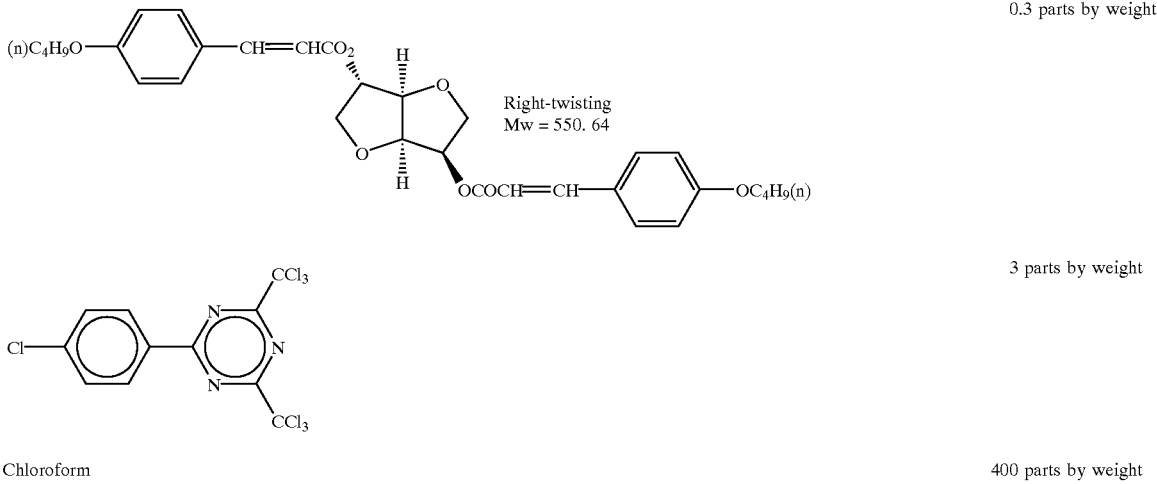

Right-twisting
Mw = 550. 64

Chloroform | 400 parts by weight 3 parts by weight

Next, the film was polymerized to be hardened by irradiation over the film with ultraviolet radiation using an high pressure mercury lamp (irradiation energy 1000 mJ/cm$^2$) at 100° C., to produce an optical compensation film for an STN element (hereinafter, referred to as "STN compensation film"). The film thickness of the STN compensation film as this stage was measured and was found to be 5.0 μm. From the polarization transmission spectrum profile of the STN compensation film, it was found that the orientation (helical structure) of liquid crystal molecules was twisted to the film thickness direction by 240° and the twist angle of the helix (rotation angle) was 240°.

Further, an STN compensation film having a twist angle of the reverse direction to that of the above-mentioned film was prepared. These were laminated such that liquid crystal molecules crossed at right angle at the joined parts, were inserted between two polarization plates having absorption axes crossing each other at right angle, and observed visually to confirm excellent black color. Therefore, it was confirmed that the film (STN compensation film) formed as described above acted as an optical compensation film for an STN element.

Example 10
Prevention of Occurrence of Reverse Twist Domain for a TN Element

On an ITO film of a glass substrate equipped with the ITO film, a polyimide orientation film (LX-1400, manufactured by Hitachi Chemical Dupont) application solution was applied by a spin coater, dried for 5 minutes in an oven at 100° C., and then baked for 1 hour in an oven at 250° C. to form an orientation film. Further, the surface of the film was subjected to orientation treatment by performing rubbing treatment so that the rubbing angle was 90°, to produce two glass substrates equipped with orientation films.

The glass substrates were placed so that the orientation films faced each other, and pasted by a two-part epoxy resin adhesive into which spacer beads having a diameter of 6 μm had been mixed, to form a cell for driving. The thickness of this cell was measured by a light interference method and was found to be 5.4 μm.

Into the above-mentioned cell, the following composition was poured. The following light-reaction type chiral agent of the present invention (exemplified compound (14)) was synthesized by the above-mentioned synthesis method.
[Composition]
Nematic liquid crystal composition (ZLI-1132, manufactured by Merck) 99.9%
Light-reaction type chiral agent of the present invention (exemplified compound (14) described previously) 0.1%

After the pouring, the cell for driving was inserted between two polarization plates whose absorption axes crossed at right angle, and observed visually, to find no occurrence of reverse twist domain. Therefore, there was no reduction in contrast by occurrence of reverse twist, and images excellent in contrast and color purities would be expected to be displayed.

What is claimed is:
1. A light-reaction type optically active compound represented by the following general formula (I):

General formula (I)

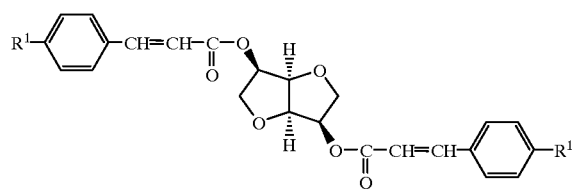

in which formula, R$^1$ represents a hydrogen atom, an alkoxy group having 1 to 15 carbon atoms, an acryloyloxyalkyloxy group having 3 to 15 carbon atoms in total, or a methacryloyloxyalkyloxy group having 4 to 15 carbon atoms in total.

2. The light-reaction type optically active compound according to claim 1, wherein in the general formula (I), R$^1$ is an acryloyloxyalkyloxy group having 3 to 15 carbon atoms in total or a methacryloyloxyalkyloxy group having 4 to 15 carbon atoms in total.

3. The light-reaction type optically active compound according to claim 1, wherein in the general formula (I), $R^1$ is a hydrogen atom or an alkoxy group having 1 to 15 carbon atoms.

4. A light-reaction type chiral agent for changing twisting power of a liquid crystal when irradiated by light, the agent comprising a compound represented by general formula (I) as follows:

General formula (I)

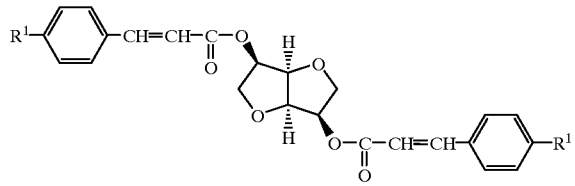

in which formula $R^1$ represents a hydrogen atom, an alkoxy group having 1 to 15 carbon atoms, an acryloyloxyalkyloxy group having 3 to 15 carbon atoms in total, or a methacryloyloxyalkyloxy group having 4 to 15 carbon atoms in total.

5. A liquid crystal composition comprising the light-reaction type optically active compound according to claim 1.

6. A liquid crystal color filter comprising the light-reaction type optically active compound according to claim 1.

7. An optical film comprising the light-reaction type optically active compound according to claim 1.

8. A recording medium comprising the light-reaction type optically active compound according to claim 1.

9. A method for changing twist structure of liquid crystals, the method comprising the steps of:

providing the liquid crystal composition according to claim 5; and irradiating the liquid crystal composition with light to cause a change of twisting power of the liquid crystals.

10. A light-reaction type chiral agent for changing twisting power of a liquid crystal when irradiated by light, the agent comprising a compound represented by general formula (II) as follows:

General formula (II)

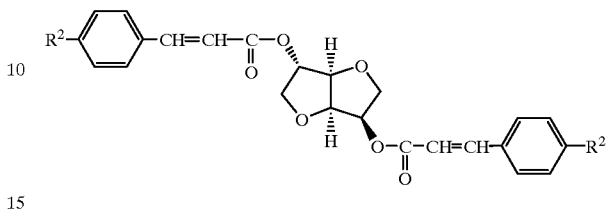

in which formula $R^2$ represents an acryloyloxyalkyloxy group having 3 to 15 carbon atoms in total, or a methacryloyloxyalkyloxy group having 4 to 15 carbon atoms in total.

11. The light-reaction type chiral agent according to claim 10, wherein in the general formula (II), $R^2$ is a hydrogen atom or an alkoxy group having 1 to 15 carbon atoms.

12. A liquid crystal composition comprising the light-reaction type chiral agent according to claim 10.

13. A method for changing twist structure of liquid crystals, the method comprising the steps of:

providing the liquid crystal composition according to claim 12; and irradiating the liquid crystal composition with light to cause a change of twisting power of the liquid crystals.

14. A liquid crystal color filter comprising the light-reaction type chiral agent of claim 10.

15. An optical film comprising the light-reaction type chiral agent according to claim 10.

16. A recording medium comprising the light-reaction type chiral agent according to claim 10.

* * * * *